(12) United States Patent
Kwak

(10) Patent No.: US 12,201,663 B2
(45) Date of Patent: Jan. 21, 2025

(54) COMPOSITION FOR ANTI-OXIDATION AND ANTI-INFLAMMATION COMPRISING SALVIA PLEBEIA R BR EXTRACT AND CENTELLA ASIATICA EXTRACT

(71) Applicant: ALL IN ON Co., Ltd, Seoul (KR)

(72) Inventor: Jong Bock Kwak, Seoul (KR)

(73) Assignee: ALL IN ON Co., Ltd, Seoul (KR)

( * ) Notice: Subject to any disclaimer, the term of this patent is extended or adjusted under 35 U.S.C. 154(b) by 129 days.

(21) Appl. No.: 17/750,125

(22) Filed: May 20, 2022

(65) Prior Publication Data

US 2023/0059068 A1 Feb. 23, 2023

(30) Foreign Application Priority Data

Aug. 17, 2021 (KR) .......................... 10-2021-107972

(51) Int. Cl.
| | | |
|---|---|---|
| A61K 36/00 | (2006.01) | |
| A61K 8/9789 | (2017.01) | |
| A61K 36/23 | (2006.01) | |
| A61K 36/537 | (2006.01) | |
| A61P 17/04 | (2006.01) | |
| A61Q 19/02 | (2006.01) | |

(52) U.S. Cl.
CPC .......... *A61K 36/537* (2013.01); *A61K 8/9789* (2017.08); *A61K 36/23* (2013.01); *A61P 17/04* (2018.01); *A61Q 19/02* (2013.01); *A61K 2236/331* (2013.01); *A61K 2236/333* (2013.01); *A61K 2236/35* (2013.01)

(58) Field of Classification Search
CPC ................................ A61Q 19/00; A61P 17/00
See application file for complete search history.

(56) References Cited

FOREIGN PATENT DOCUMENTS

| CN | 104771461 A | * | 7/2015 |
|---|---|---|---|
| KR | 10-2007-0016261 A | | 2/2007 |

\* cited by examiner

*Primary Examiner* — Qiuwen Mi
(74) *Attorney, Agent, or Firm* — Heedong Chae; Lucem, PC

(57) ABSTRACT

The present invention relates to a composition for anti-oxidation and anti-inflammation, comprising a *Salvia plebeia* R. BR. extract and a *Centella asiatica* extract as an active ingredient. The composition exhibits a radical scavenging ability, and has excellent antioxidant, anti-inflammatory and anti-itching effects by significantly inhibiting inflammation and itch-inducing factors at gene and protein levels, and thus can be advantageously used as a cosmetic composition for anti-oxidation and anti-inflammation.

6 Claims, 24 Drawing Sheets

Specification includes a Sequence Listing.

COMPOSITION FOR ANTI-OXIDATION AND ANTI-INFLAMMATION COMPRISING SALVIA PLEBEIA R BR EXTRACT AND CENTELLA ASIATICA EXTRACT

CROSS-REFERENCE TO RELATED APPLICATIONS

This application claims the priority of Korean Patent Application No. 10-2021-107972 filed on Aug. 17, 2021, in the Korean Intellectual Property Office, the disclosure of which is incorporated herein by reference.

REFERENCE TO SEQUENCE LISTING

Pursuant to the EFS-Web legal framework and 37 C.F.R. §§ 1.821-825), a Sequence Listing in the form of an ASCII-compliant text file (entitled "7041PAT220_Sequencelisting_ST25.txt" created on Nov. 13, 2024 having a size of 2.97 KB) is submitted herewith the instant application, and the entire contents of the Sequence Listing are incorporated herein by reference.

TECHNICAL FIELD

The present invention relates to a composition for anti-oxidation and anti-inflammation, including a *Salvia plebeia* R. BR. extract and a *Centella asiatica* extract as an active ingredient.

BACKGROUND ART

An inflammatory response is a defensive response that occurs when a living tissue is damaged, and is a series of immune responses that are inevitably caused by activated immune cells. In the inflammatory response, inflammatory mediators such as nitric oxide (NO), pro-inflammatory cytokines, prostaglandin E2 (PGE2) and the like are produced by activating immune cells. Accordingly, it is known that free radicals such as reactive oxygen species are accompanied to induce a secondary reaction.

Meanwhile, the free radicals accumulate in cells and damage the cells due to high reactivity, which impedes the growth or proliferation of cells and slows the regeneration of damaged skin cells, thus resulting in secondary skin lesions such as wounds, rashes, etc., and itchiness. In addition, due to abnormalities in metabolic processes in the body, aging such as skin pigmentation, loss of elasticity, etc., may be accelerated.

Thus, inhibiting the production of NO or PGE2 and the expression of inflammatory cytokines and inhibiting the production of free radicals from inflammation become key targets in the treatment of inflammatory diseases. In general, steroidal anti-inflammatory drugs used to treat inflammatory diseases have disadvantages of not only causing diseases such as glaucoma, cataracts, high blood pressure, bipolar disorder, weight gain, diabetes, osteoporosis, etc., but also decreasing anti-oxidant activity. Accordingly, there is a need to develop a material that does not have or minimizes the risk of side effects or cytotoxicity, and for this purpose, research using natural materials is being actively conducted.

RELATED ART REFERENCES

Patent Documents (Patent Document 0001) Korean Unexamined Patent Application No. 10-2007-0016261

DISCLOSURE

Technical Problem

To solve the above problems, an object of the present invention is to provide a composition including a *Salvia plebeia* R. BR. and *Centella asiatica* extract, having an excellent anti-oxidant and anti-inflammatory efficacy.

In addition, an object of the present invention is to provide a cosmetic composition including the composition.

Technical Solution

*Salvia plebeia* R. BR. is also called *Salvia plebeia* R. Brown or Plebeian sage, and although it is an annual plant, *Salvia plebeia* R. BR. has a feature of having a strong stem like a bamboo when it is grown up. *Salvia*, a generic name, comes from the Latin word "salvare," and most of the species belonging to *Salvia* are used for medicinal or edible purposes. According to recent studies, it has been found that *Salvia plebeia* R. BR. contains strong antioxidants. However, due to strong cytotoxicity, caution is required when being used for medicinal or edible purposes.

*Centella asiatica* is a perennial plant commonly grown in mountains or fields in Korea, and is mainly distributed in Asian regions such as Japan, China, etc. Recently, *Centella asiatica* is used in the preparation of antibacterial cosmetics as it has an antibacterial effect against bacteria, fungi, etc., but also has a disadvantage in that it is difficult to expect a great antibacterial effect when used alone.

Above *Salvia plebeia* R. BR. and *Centella asiatica* have been reported to have antioxidant or anti-inflammatory effects by some studies, but there has been no study on the cytotoxic, antioxidant and anti-inflammatory effects of mixtures thereof.

Thus, in the present invention, the composition may have a feature of being safe and exhibiting excellent antioxidant and anti-inflammatory effects because cytotoxicity is supplemented by including the *Salvia plebeia* R. BR. extract and the *Centella asiatica* extract at an optimal ratio as active ingredients.

One aspect of the present invention may provide a composition for anti-oxidation and anti-inflammation, including a *Salvia plebeia* R. BR. extract and a *Centella asiatica* extract as an active ingredient.

The "*Salvia plebeia* R. BR. extract" and the "*Centella asiatica* extract" used in the present invention may include an extract liquid per se and all the formulations of extracts which may be formed by using the extract liquid, such as an extract liquid obtained by using *Salvia plebeia* R. BR. and *Centella asiatica* alone or in combination and subjecting to an extraction, a diluent or concentrate of the extract liquid, a dried matter obtained by drying the extract liquid, a crude purified product or a purified product of the extract liquid, a mixture thereof, or the like.

The *Salvia plebeia* R. BR. extract and the *Centella asiatica* extract used herein may include *Salvia plebeia* R. BR. and *Centella asiatica* which are collected in nature or commercially grown and sold. In this case, the *Salvia plebeia* R. BR. and the *Centella asiatica* may be unprocessed in a state of nature or may be in a state in which the *Salvia plebeia* R. BR. and the *Centella asiatica* have undergone processing such as freezing, drying, etc. And, the *Salvia plebeia* R. BR. and the *Centella asiatica* may be obtained by using selectively or all of the flowers, leaves, petioles, stems, roots, etc. of the *Salvia* plebeia R. BR. or the *Centella asiatica*, but is not limited thereto.

According to one specific embodiment of the present invention, the extract may be obtained by using an extraction method known in the art without limitation. The extraction method may include, as one example, a cold extraction, an ultrasonic extraction, a reflux cooling extraction, a hot water extraction, a pressure extraction, a solvent extraction, and the like, and a combination of two or more extraction methods may be used for effective extraction of active ingredients.

According to one specific embodiment of the present invention, the extract may be obtained by extracting with a solvent selected from water, alcohol having 1 to 4 carbon atoms, propylene glycol, butylene glycol, glycerin, acetone, ethyl acetate, butyl acetate, chloroform, diethyl ether, dichloromethane, hexane and mixtures thereof.

According to one specific embodiment of the present invention, the extract may be prepared in a powder state by an additional process such as concentration under reduced pressure and freeze-drying, spray-drying or the like.

According to one specific embodiment of the present invention, the extract may include not only an extract by the above-described extraction method, but also an extract that has undergone a conventional purification process. For example, fractions obtained through various further purification methods such as separation using an ultrafiltration membrane having a constant molecular weight cut-off value, separation by various chromatographies (prepared for separation according to size, charge, hydrophobicity or affinity), etc., may also be included in the extract of the present invention.

According to one embodiment of the present invention, above *Salvia plebeia* R. BR. extract and *Centella asiatica* extract may be obtained by mixing *Salvia plebeia* R. BR. and *Centella asiatica* with a solvent 5 to 20 times thereof (preferably the solvent 10 to 15 times thereof), subjecting to an extraction under reflux for 0.5 to 8 hours (preferably 1 to 5 hours), concentrating the filtrate under reduced pressure, and freeze-drying.

The *Salvia plebeia* R. BR. extract and the *Centella asiatica* extract may be used as a composition mixed at an appropriate ratio in order to supplement the cytotoxicity of the two extracts and exhibit an excellent anti-inflammatory efficacy.

According to one specific embodiment of the present invention, the composition may be obtained by mixing the *Salvia plebeia* R. BR. extract and the *Centella asiatica* extract at a weight ratio of 5 to 10:1 to 5.

More specifically, the mixing ratio of the *Salvia plebeia* R. BR. extract and the *Centella asiatica* extract may be 7:3 by weight.

In this case, when the ratio of the *Salvia plebeia* R. BR. extract is less than a lower limit, cytotoxicity is not strong, but an excellent anti-inflammatory effect cannot be expected because the extract cannot effectively inhibit the generation of nitric oxide that causes inflammation. When the ratio exceeds an upper limit, strong cytotoxicity may be exhibited due to an insufficient cytoprotective effect.

The composition may contain a large amount of total flavonoids and polyphenols to exhibit excellent DPPH and ABTS radical scavenging activities, inhibit the expression and secretion of inflammation-related factors such as NO, PGE2, inflammatory cytokines (IL-1$\beta$, IL-6 and TNF-a), and NF-$\kappa$B activities, and inhibit the secretion of related factors such as cytokines, histamine, etc., which cause itchiness, and thus can be advantageously used as an anti-oxidant, anti-inflammatory and anti-itching composition. The composition according to one specific embodiment of the present invention may provide an anti-oxidant, anti-inflammatory and anti-itching composition including a *Salvia plebeia* R. BR. extract and a *Centella asiatica* extract as an active ingredient.

As used herein, "anti-oxidant" may refer to an action of inhibiting oxidation, and when oxidative stress is induced, potential cell damage and pathological diseases may occur. Reactive oxygen species, which are a direct cause of oxidative stress, are unstable and highly reactive, and thus easily react with various biomaterials and attack macromolecules in the body, thereby causing an irreversible damage to cells and tissues or causing mutations, cytotoxicity, carcinogenesis, and the like.

As used herein, "anti-inflammatory" may mean inhibiting a process of inflammation or a substance involved therein, and in order to produce an anti-inflammatory effect, it is a key to inhibit or control an expression of inflammatory cytokines such as NO or PGE2, IL-1$\beta$ and TNF-a acting on the inflammatory response.

As used herein, "anti-itching" may mean alleviating or relieving itchiness, which occurs most predominantly in skin diseases. Itchiness may be accompanied by pain and may result from various causes, which lead to secondary skin lesions such as wounds, rashes, etc. Scratching resulting from itchiness may lead to a vicious circle of secreting substances that cause itchiness, thus exacerbating itchiness. Inhibiting or controlling the expression of IL-4, IL-31, and histamine, which are known to cause itchiness, may be a key to treatment of itchiness.

According to one embodiment of the present invention, the composition may contain total polyphenols amount of 10.367±0.51 mg GAE/g and total flavonoids in an amount of 37.98±2.39 mg QE/g, and thus may exhibit excellent DPPH and ABTS radical scavenging abilities without any cytotoxicity, and significantly inhibit the expression of nitric oxide, prostaglandin, IL-1$\beta$, IL-6 and TNF-a secreted by immune cells and the expression of IL-4, IL-31 and histamine secreted by mast cells at gene and protein levels.

The composition may be used for the purpose of alleviating itchiness of the whole body including the skin. For example, the composition may be used as a shampoo, body cleanser, soap, foam cleanser, skin, lotion, cream, ointment, spray, toothpaste, wet tissue, animal wet tissue, pet cleaner, fabric softener, lens cleaner, feminine cleanser, etc.

According to one specific embodiment of the present invention, the composition may be a composition for skin, scalp, oral cavity, eye or vagina.

Another aspect of the present invention may provide a cosmetic composition for anti-oxidation and anti-inflammation including the composition.

According to one specific embodiment of the present invention, the cosmetic composition may contain a large amount of antioxidants and effectively suppress the expression of IL-4, IL-31 and histamine, which are itch-inducing factors, thereby alleviating or relieving skin itchiness.

In addition, according to one specific embodiment of the present invention, the cosmetic composition may contain a large amount of antioxidants and may effectively inhibit the production of melanin, a skin pigment, thereby brighten a skin tone.

The cosmetic composition according to the present invention may be prepared as a formulation selected from the group consisting of solution, external ointment, cream, foam, nutrient lotion, softening lotion, pack, soft water, emulsion, makeup base, essence, soap, liquid detergent, bathing agent, sunscreen cream, sun oil, suspension, emulsion, paste, gel, lotion, powder, soap, surfactant-containing cleansing, oil, powder foundation, emulsion foundation, wax foundation, patch and spray, but is not limited thereto.

According to one specific embodiment of the present invention, the cosmetic composition may further include one or more cosmetically acceptable carriers to be compounded in general skin cosmetics, and as common ingredients, for example, oil, water, surfactant, moisturizer, lower alcohol, thickener, chelating agent, colorant, preservative, fragrance, etc., may be appropriately compounded, but the present invention is not limited thereto.

According to one specific embodiment of the present invention, the cosmetically acceptable carriers included in the cosmetic composition may vary depending on formulations.

If a formulation of the cosmetic composition according to one specific embodiment of the present invention is ointment, paste, cream or gel, then animal oil, vegetable oil, wax, paraffin, starch, tragacanth, cellulose derivative, polyethylene glycol, silicon, bentonite, silica, talc, zinc oxide, or mixtures thereof may be used as a carrier ingredient.

If a formulation of the cosmetic composition according to one specific embodiment of the present invention is a powder or spray, then lactose, talc, silica, aluminum hydroxide, calcium silicate, polyamide powder or mixtures thereof may be used as a carrier component. In particular, in the case of a spray, propellants such as chlorofluorohydrocarbon, propane/butane or dimethyl ether may be further included.

If a formulation of the cosmetic composition according to one specific embodiment of the present invention is a solution or emulsion, then a solvent, solubilizer or emulsifier may be used as a carrier component. For example, water, ethanol, isopropanol, diethyl carbonate, ethyl acetate, benzyl alcohol, benzyl benzoate, propylene glycol, and 1,3-butylene glycol oil may be used, and in particular, cottonseed oil, peanut oil, corn germ oil, olive oil, castor oil and sesame oil, glycerol aliphatic ester, and fatty acid esters of polyethylene glycol or sorbitan may be used.

If a formulation of the cosmetic composition according to one specific embodiment of the present invention is a suspension, then a liquid diluent such as water, ethanol or propylene glycol, as a suspending agent such ethoxylated isostearyl alcohol, polyoxyethylene sorbitol ester and polyoxyethylene sorbitan ester, microcrystalline cellulose, aluminum metahydroxide, bentonite, agar, tragacanth or the like may be used.

In addition, another aspect of the present invention may provide a pharmaceutical composition for preventing or treating inflammatory diseases, including the composition for anti-oxidation and anti-inflammation.

According to one specific embodiment of the present invention, the itchiness may be at least one selected from the group consisting of dermatitis, allergy, vaginitis, atopy, asthma, conjunctivitis, cataract, periodontitis, rhinitis, otitis media, sore throat, tonsillitis, pneumonia, sepsis, gastric ulcer, gastritis, Crohn's disease, hemorrhoids, ankylosing Spondylitis, lupus, fibromyalgia, psoriasis, arthritis, osteoarthritis, rheumatoid arthritis, periarteritis, tendinitis, tenosynovitis, myositis, hepatitis, cystitis, nephritis, multiple sclerosis, diabetes, scleroderma, gout, neurodegenerative disease, silicosis, atherosclerosis and ischemia.

The pharmaceutical composition of the present invention may further include pharmaceutically acceptable additives. The additives may include starch, gelatinized starch, microcrystalline cellulose, lactose, povidone, colloidal silicon dioxide, hydroxycalcium phosphate, lactose, mannitol, taffy, gum arabic, pregelatinized starch, corn starch, powdered cellulose, hydroxypropylcellulose, opadry, sodium starch glycolate, lead carnauba, synthetic aluminum silicate, stearic acid, magnesium stearate, aluminum stearate, calcium stearate, sucrose, dextrose, sorbitol and talc, but is not limited thereto.

The pharmaceutical composition according to one specific embodiment of the present invention may further include a pharmaceutically acceptable carrier. The carrier may be one which is conventionally used in formulating a preparation, including, but not limited thereto, lactose, dextrose, sucrose, sorbitol, mannitol, trehalose, hyaluronic acid, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, mineral oil, and the like.

The pharmaceutical composition according to one specific embodiment of the present further invention may include lubricant, humectant, a sweetening agent, a flavoring agent, emulsifier, a suspending agent, preservative, etc. Suitable pharmaceutically acceptable carriers and preparations are described in detail in Remington's Pharmaceutical Sciences (22th ed., 2013).

The pharmaceutical composition of the present invention may be administered in various oral and parenteral dosage forms upon an actual clinical administration. When being formulated into a preparation, the composition may be prepared by using the generally used diluents or excipients such as fillers, diluents, extenders, binders, humectants, disintegrants, surfactants, etc. A solid preparation for oral administration may include tablets, pills, powders, granules, capsules, etc., and this solid preparation may be prepared by mixing at least one excipient, for example, starch, calcium carbonate, sucrose, lactose, gelatin, or the like in a herbal medicine composition with an increased fat-soluble polyphenol component of the present invention. In addition, lubricants such as magnesium stearate and talc may be also used in addition to simple excipients.

The pharmaceutical composition of the present invention may be orally or parenterally administered according to a desired method, and when parenterally administered, intraperitoneal injection, rectal injection, subcutaneous injection, intravenous injection, intramuscular injection, or intrathoracic injection methods may be selected. A dosage may vary in a range thereof depending on a patient's weight, age, gender, health condition and diet, an administration time, an administration method, an excretion rate, a severity of a disease and the like.

The pharmaceutical composition of the present invention may be administered in a pharmaceutically effective amount. In the present invention, "pharmaceutically effective amount" may mean an amount enough to treat a disease at a reasonable benefit/risk ratio applicable to medical treatment, and a level of effective amount may be determined according to factors including a patient's disease type, severity, activity of a drug, the drug, an administration time, an sensitivity to administration route and excretion rate, a treatment period and a concurrently used drug, as well as other factors well known in a medical field. The composition according to one specific embodiment of the present invention may be administered as an individual therapeutic agent or in combination with other therapeutic agents, may be administered sequentially or simultaneously with a conventional therapeutic agent, and may be administered in a single or multiple manner. Considering all the factors above, it is important to carry out an administration by an amount, in which the maximum effect may be achieved by the minimum amount without a side effect, in which such amount may be easily determined by those skilled in the art.

Specifically, an effective amount of the pharmaceutical composition according to one specific embodiment of the present invention may vary depending on a patient's age, gender and weight, and may be generally administered in an amount of 0.001 mg to 1,000 mg, 0.01 mg to 100 mg, or 0.1 mg to 10 mg per 1 kg of body, which may be administered everyday or every other day, or administered at one time to three times a day by dividing the daily dosage of the composition. However, the effective amount may increase route of or decrease depending on the administration, the severity of disease, gender, weight, age, etc., and thus the dosage may not be intended to limit the scope of the present invention in any way.

Advantageous Effects

According to the present invention, the composition including a Salvia plebeia R. BR. extract and a Centella asiatica extract can exhibit a radical scavenging ability, and has excellent anti-oxidant, anti-inflammatory and anti-itching effects by significantly inhibiting inflammation and itch-inducing factors at gene and protein levels, and thus can be advantageously used as a cosmetic composition for anti-oxidation and anti-inflammation.

MODE FOR INVENTION

Figure 1:
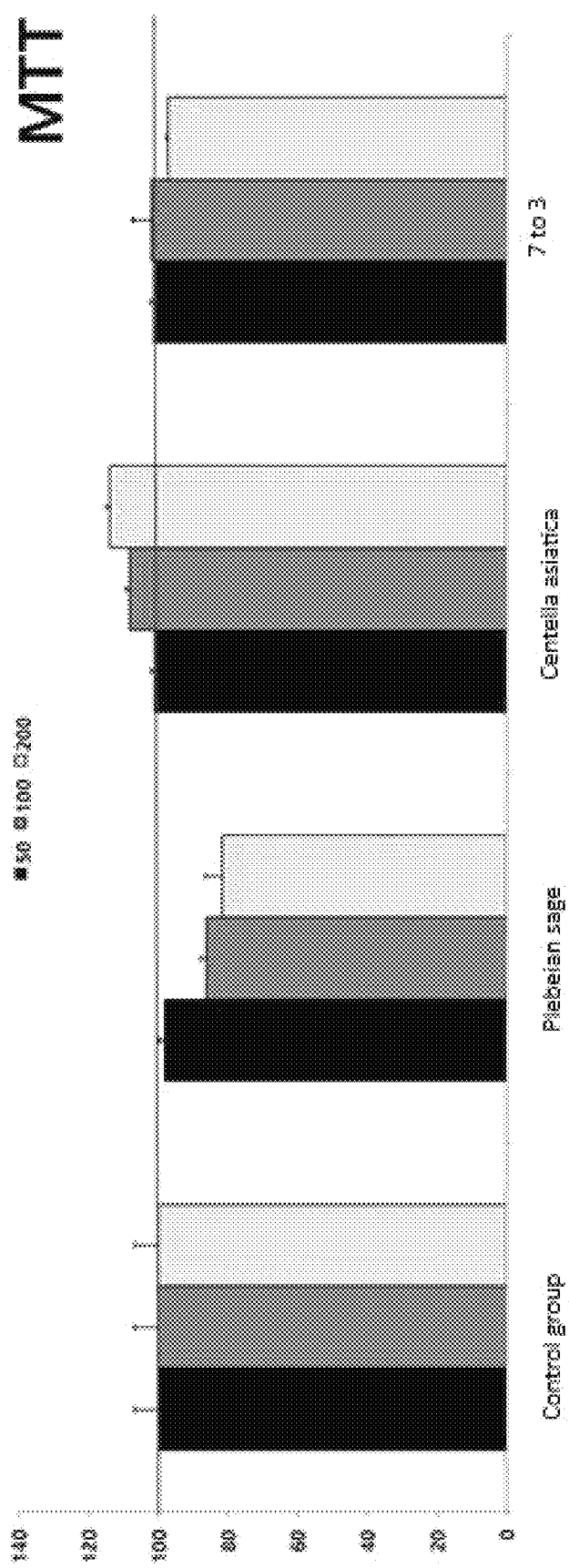
FIG. 1 is a result of measuring cell viability according to a mixing ratio of Salvia plebeia R. BR. extract and Centella asiatica extract according to one embodiment of the present invention.

Hereinafter, the present invention will be described in more detail with reference to the accompanying drawings. However, the description is provided only for the purpose of illustrating the present invention, and thus the scope of the present invention is not limited to the exemplary description.

Example 1. Preparation of *Salvia plebeia* R. BR. Extract

*Salvia plebeia* R. BR. was grown wild at Keungol, Baekokpo-ri in Pyeongchang and harvested in July 2020. Leaves, including stems, were freeze-dried at −4° C. for two days and used as a raw material. After that, 500 ml of 70% ethanol was added to 40 g of *Salvia plebeia* R. BR., and extracted under reflux for three hours, after which the filtrate was concentrated under reduced pressure with a rotary vacuum evaporator (EYELA FDU-540, Japan) and the concentrated solution was freeze-dried with a freeze dryer (Ilshin Biobase, Korea) to obtain a *Salvia plebeia* R. BR. ethanol extract. 3.84 g of powder was obtained (yield of 9.60%) as a *Salvia plebeia* R. BR. extract, and was diluted in distilled water to a concentration required for an experiment while being stored in a cryogenic freezer (−80° C.).

Example 2. Preparation of *Centella asiatica* Extract

*Centella asiatica* was grown wild at Keungol, Baekokpo-ri in Pyeongchang and harvested in July 2020. *Centella asiatica* leaves, including petioles, were freeze-dried at −4° C. for two days and used as a raw material. After that, 500 ml of 70% ethanol was added to 40 g of *Centella asiatica* and extracted under reflux for three hours, after which the filtrate was concentrated under reduced pressure with a rotary vacuum evaporator (EYELA FDU-540, Japan) and the concentrated solution was freeze-dried with a freeze dryer (Ilshin Biobase, Korea) to obtain a *Centella asiatica* ethanol extract. 3.84 g of powder was obtained (yield of 9.60%) as a *Centella asiatica* extract, and was diluted in distilled water to a concentration required for an experiment while being stored in a cryogenic freezer (−80° C.).

Experimental Example 1. Optimal Mixing Ratio of *Salvia plebeia* R. BR. Extract and *Centella asiatica* Extract Each extract and mixtures thereof were used to analyze cytotoxicity and anti-inflammatory efficacy, in order to set an optimal mixing ratio of a *Salvia plebeia* R. BR. extract and a *Centella asiatica* extract.

1-1. Cytotoxicity

To measure cytotoxicity, an MTT assay was performed. RAW264.7 cells were cultured in a cell incubator maintained at 37° C. and under 5% CO2 conditions using a DMEM medium (Gibco BRL, USA) containing 10% FBS and 1% penicillin-streptomycin and an experiment was carried out by subculture at a cycle of 2-3 days.

After that, RAW264.7 cells were seeded in a 96-well plate at $2\times10^5$ cells/well and cultured for 24 hours. In 24 hours later, the *Salvia plebeia* R. BR. extract and the *Centella asiatica* extract were mixed alone or at a ratio of 7:3, treated at a concentration of 50, 100, and 200 μg/ml, and cultured for another 24 hours. In 24 hours later, 20 μL of MTT solution (5 mg/ml) was added to each well and incubated in a CO2 cell incubator at 37° C. for four hours. After that, $10^8$ μL of cell culture fluid was obtained and 180 μL of methanol/DMSO (1:1) solution was added to each well and mixed in a shaker, after which absorbance was measured at 540 nm to determine cell viability relative to the control group and indicate the same as a percentage.

As a result, referring to FIG. 1, the *Salvia plebeia* R. BR. extract exhibited at least 80% apoptosis at a concentration of 50 ug/ml or more, whereas the *Centella asiatica* extract rather exhibited cell protection at a concentration of 100 ug/ml or more, which may be expected to provide a cell regeneration effect.

Meanwhile, in the case of treating with the *Salvia plebeia* R. BR. extract and the *Centella asiatica* extract at a ratio of 7:3, it was found that the cytotoxicity is alleviated by the *Centella asiatica* extract.

1-2. Anti-Inflammatory Efficacy

In order to measure an amount of NO production as an index of anti-inflammatory efficacy, a NO analysis kit (Intronbio, Korea) was used. RAW264.7 cells were seeded in a 24-well plate at $4\times10^4$ cells/well and cultured for 24 hours, after which the extract was treated at a concentration of 50, 100, and 200 μg/ml, treated with 100 ng/ml of LPS in two hours later, and cultured again for 24 hours. After incubation, 100 μl of the cell culture fluid was added to a 96-well plate, after which 50 μl of N1 buffer was added and reacted at room temperature for 10 minutes. After the reaction, 50 μl of N2 buffer was added and reacted at room temperature for 10 minutes. After the reaction, a change in absorbance at 540 nm was measured, and a production amount relative to the control group was expressed as a percentage.

Figure 2:
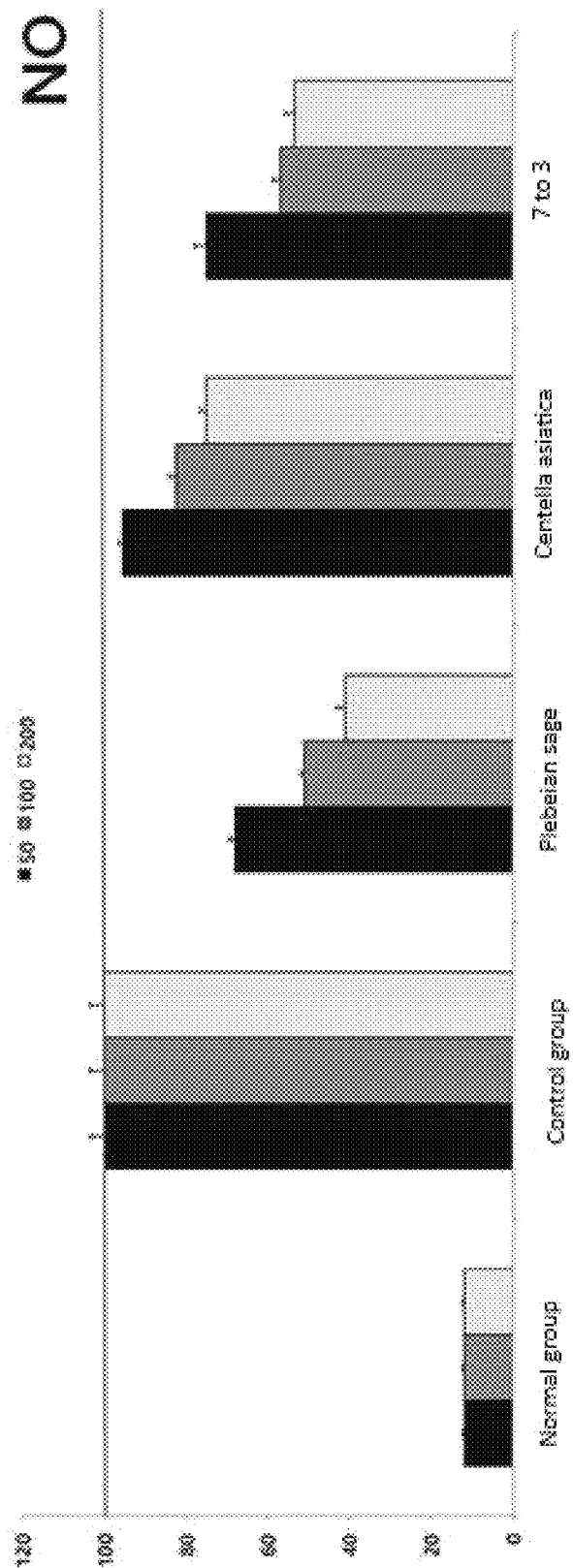
FIG. 2 is a result of measuring an amount of NO production according to a mixing ratio of Salvia plebeia R. BR. extract and Centella asiatica extract according to one embodiment of the present invention.

As a result, referring to FIG. 2, it was found that the *Salvia plebeia* R. BR. extract and the *Centella asiatica* extract inhibit NO production in a concentration-dependent manner, respectively, but the inhibition of NO production by the *Centella asiatica* extract is weaker than that of the *Salvia plebeia* R. BR. extract.

However, in the case of treating with the *Salvia plebeia* R. BR. extract and the *Centella asiatica* extract at a ratio of 7:3, it was found that the inhibition of NO production is higher than that of the *Centella asiatica* alone, indicating that an anti-inflammatory effect is improved.

From the above results, the mixed use of the *Salvia plebeia* R. BR. extract and the *Centella asiatica* extract at a ratio of 7:3 is effective in alleviating the cytotoxicity caused by the *Salvia plebeia* R. BR. extract and improving the inhibition of NO production by the *Centella asiatica* extract, and thus it may be expected to provide excellent anti-oxidant and anti-inflammatory effects.

In a subsequent experiment, a mixture of the *Salvia plebeia* R. BR. extract and the *Centella asiatica* extract at a ratio of 7:3 (hereinafter referred to as "SCE") was used.

Experimental Example 2. Total Polyphenol and Flavonoid Content of *Salvia plebeia* R. BR. And *Centella asiatica* Mixture To measure total polyphenols, 0.5 ml of 50% folin-Ciocalteu's phenol reagent (Merck, Germany) was added to 1 ml of the SCE (at a concentration of 20 mg/ml) and reacted at room temperature for three minutes. To the reaction solution, 1 ml of saturated Na2CO3 solution and 7.5 ml of distilled water were sequentially mixed, left to stand for 30 minutes, and centrifuged at 14,000 g for 10 minutes, after which the supernatant was taken and absorbance was measured at a wavelength of 760 nm. A total phenol content was calculated according to a calibration curve prepared by using gallic acid (GAE, Sigma, USA) as a standard material.

To measure total flavonoids, 0.1 ml of 10% aluminum nitrate and 1M potassium acetate and 4.3 ml of 80% ethanol were added to 0.5 ml of a mixture of 0.1 ml of the SCE (at a concentration of 20 mg/ml) and 0.9 ml of 80% ethanol and left to stand for 40 minutes at room temperature, after which absorbance was measured at a wavelength of 415 nm, and a content was obtained from a standard curve prepared by using quercetin (QE).

As a result, a total polyphenol content of the SCE was 103.67±0.51 mg GAE/g, and a total flavonoid content was 37.98±2.39 mg QE/g.

Experimental Example 3. Anti-Oxidant Efficacy of *Salvia plebeia* R. BR and *Centella asiatica*

In order to evaluate an anti-oxidant power of the *Salvia plebeia* R. BR. and *Centella asiatica* mixture, a radical scavenging ability was measured.

3-1. DPPH Radical Scavenging Ability

Dilution was performed with distilled water so that a final concentration of the SCE could reach 25, 50, 100, 250, 500 and 1000 µg/ml, and 150 ul of 0.2 mM DPPH (1,1-diphenyl-2-picryl-hydrazyl) solution and 100 µl of each sample were mixed and reacted at 37° C. for 30 minutes. After the reaction, absorbance was measured at a wavelength of 517 nm through a micro plate reader (Molecular Devices, U.S.A). Ascorbic acid was added as a positive control group of the sample, distilled water was added as a negative control group, and ethanol was added as a control group of the DPPH solution, so as to obtain a correction value. A DPPH free radical scavenging rate was calculated according to equation 1 below.

$$\text{Scavenging rate (\%)} = \left(\frac{\text{Absorbance of sample addition group} - \text{Absorbance of control}}{\text{Absorbance of sample addition group}}\right) \times 100 \quad \text{[Equation 1]}$$

Figure 3:
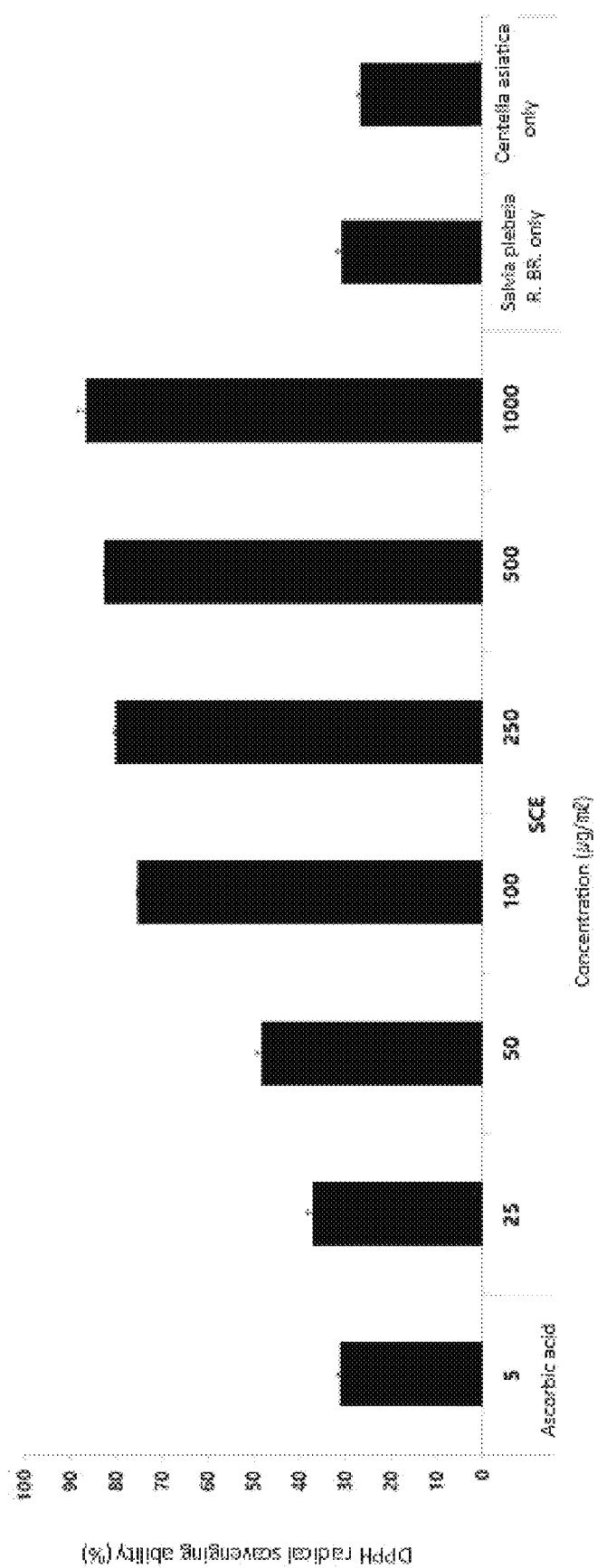
FIG. 3 is a result of measuring a DPPH radical scavenging ability by a mixture of Salvia plebeia R. BR. and Centella asiatica according to one embodiment of the present invention.

As a result, referring to FIG. 3, a DPPH radical scavenging ability of the SCE was increased in a concentration-dependent manner, and it was confirmed that an $IC_{50}$ value is 61.54 µg/ml.

In addition, the same experiment was further carried out for each individual composition of the *Salvia plebeia* R. BR. extract alone (1000 µg/ml) of Example 1 and the *Centella asiatica* extract alone (1000 µg/ml) of Example 2 and compared together as shown in FIG. 3.

3-2. ABTS Radical Scavenging Ability

Dilution was performed so that a final concentration of the SCE could reach 25, 50, 100, 250, 500 and 1000 µg/ml. As for an ABTS solution, 7.4 mM ABTS (2,2-azino-bis-(3-ethylbenzothiazoline-6-sulfonic acid)) and 2.6 mM potassium persulphate were mixed and left to stand for one day in a dark place so to form cations (ABTS+). Then, dilution was performed with distilled water so that an absorbance value could be 1.5 or less when measured at 732 nm, after which 150 µl of the diluted ABTS+ solution and 5 µl of the sample were mixed and reacted at room temperature for 10 minutes, and then absorbance was measured at a wavelength of 732 nm through a microplate reader. With regard to an anti-oxidant activity of the SCE, as shown in equation 2 below, an ABTS radical scavenging ability was expressed as a percentage relative to a control group by using distilled water as the control group.

$$\text{Scavenging rate (\%)} = \left(1 - \frac{\text{Absorbance of control}}{\text{Absorbance of sample addition group}}\right) \times 100 \quad \text{[Equation 2]}$$

Figure 4:
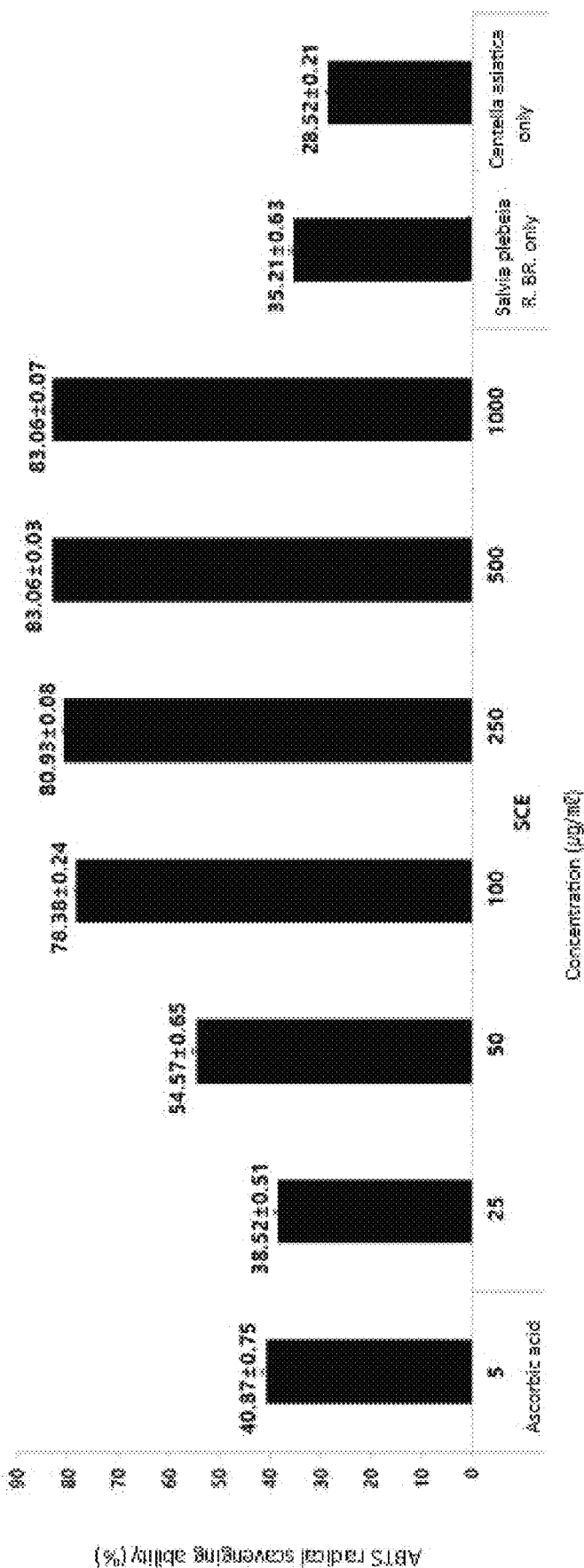
FIG. 4 is a result of measuring an ABTS radical scavenging ability by a mixture of Salvia plebeia R. BR. and Centella asiatica according to one embodiment of the present invention.

As a result, referring to FIG. 4, a ABTS radical scavenging ability of the SCE was increased in a concentration-dependent manner, and it was confirmed that an $IC_{50}$ value is 46.94 µg/ml.

In addition, the same experiment was further carried out for each individual composition of the *Salvia plebeia* R. BR. extract (1000 µg/ml) of Example 1 *Centella asiatica* extract alone (1000 µg/ml) of Example 2 and compared together as shown in FIG. 4.

Experimental Example 4. Anti-Inflammatory Efficacy of *Salvia plebeia* R. BR and *Centella asiatica*

RAW264.7 cells, macrophages, were used as immune cells to make a measurement for the *Salvia plebeia* R. BR. and *Centella asiatica* mixture in terms of cytotoxicity and the gene and protein expression amounts and production amounts of inflammation-related factors.

4-1. Cytotoxicity

RAW264.7 cells were cultured in a cell incubator maintained at 37° C. and under 5% CO2 conditions using a DMEM medium (Gibco BRL, USA) containing 10% FBS and 1% penicillin-streptomycin and an experiment was carried out by subculture at a cycle of 2-3 days.

After that, RAW264.7 cells were seeded in a 24-well plate at $1 \times 10^5$ cells/well and cultured for 24 hours. In 24 hours later, the cells were treated with the SCE at a concentration of 50, 100, 200, and 400 g/ml, and cultured for another 24 hours. As a positive control group of the sample, the cells were treated with ascorbic acid and treated with distilled as a negative control. After incubation, 10 µl of an EZ-Cytox solution (Daeilab, Korea) was added per 100 µl of the culture fluid and reacted for 30 minutes in a cell incubator. After the reaction, a change in absorbance at 450 nm was measured, and cell viability relative to the control group was expressed as a percentage.

Figure 5:
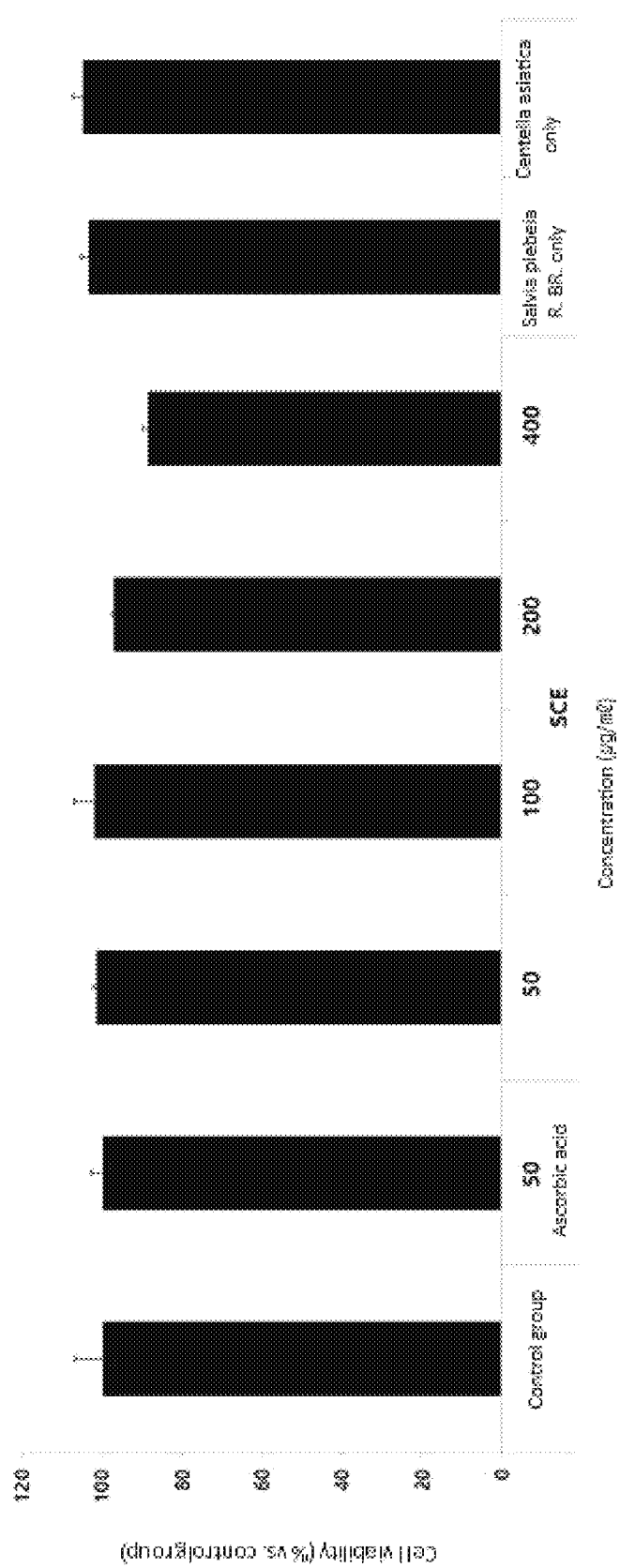
FIG. 5 is a result of measuring cell viability of RAW264.7 cells by a mixture of Salvia plebeia R. BR. and Centella asiatica according to one embodiment of the present invention.
Figure 6:
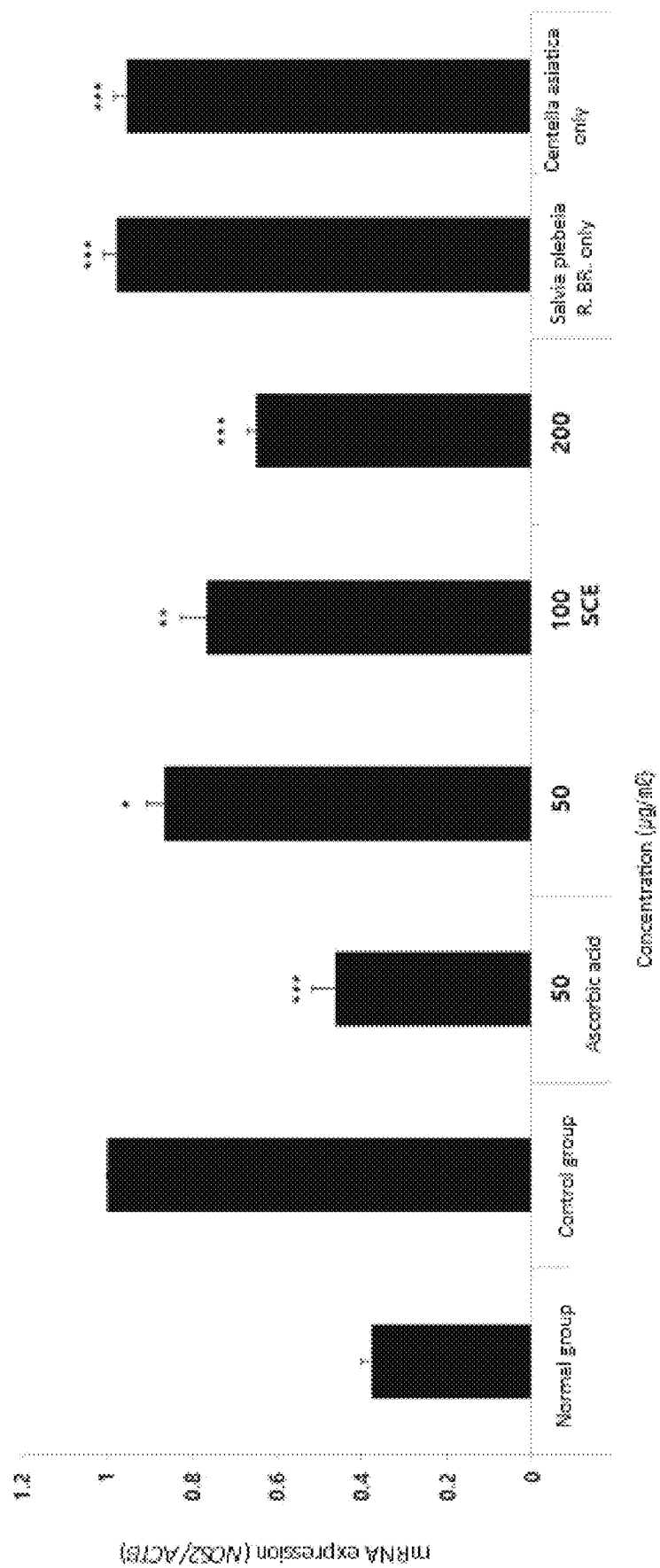
FIG. 6 is a result of measuring an mRNA expression level of NOS2 gene by a mixture of Salvia plebeia R. BR. and Centella asiatica according to one embodiment of the present invention.
Figure 7:
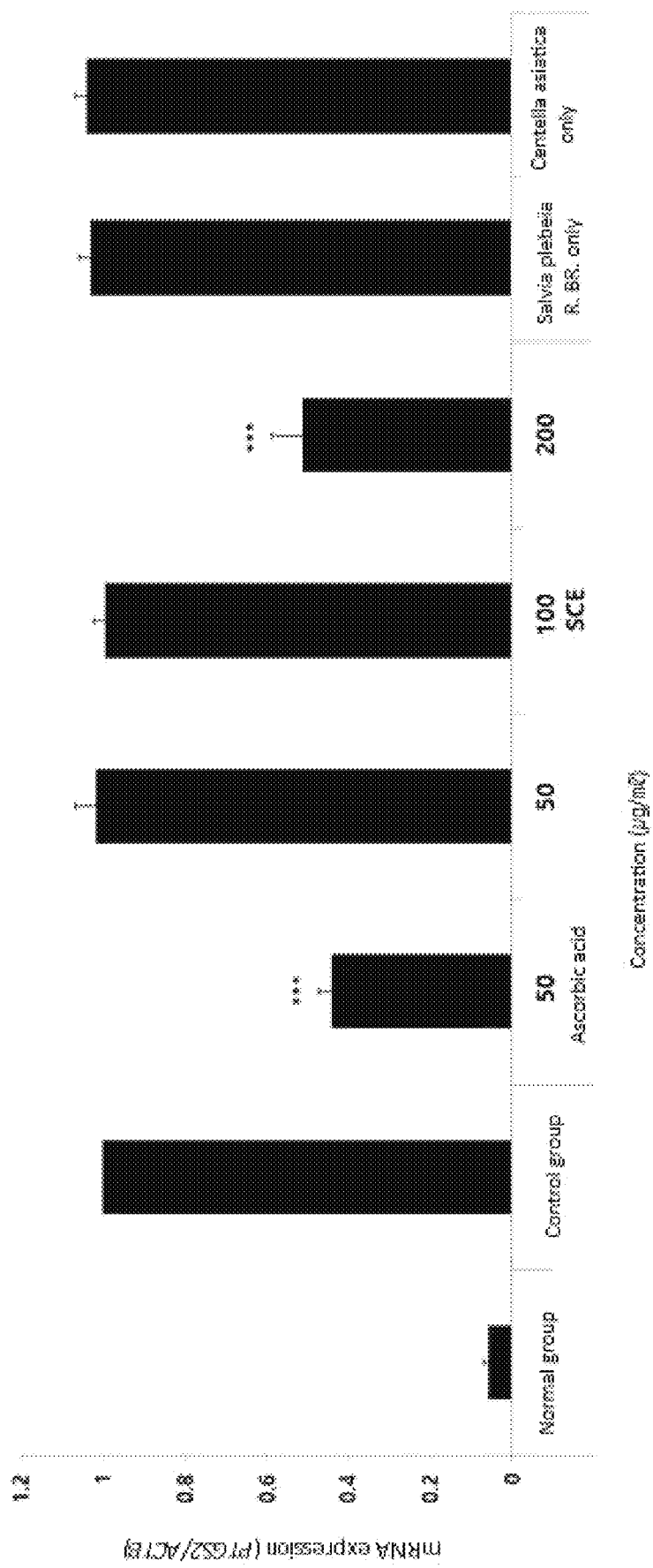
FIG. 7 is a result of measuring an mRNA expression level of PTGS2 gene by a mixture of Salvia plebeia R. BR. and Centella asiatica according to one embodiment of the present invention.
Figure 8:
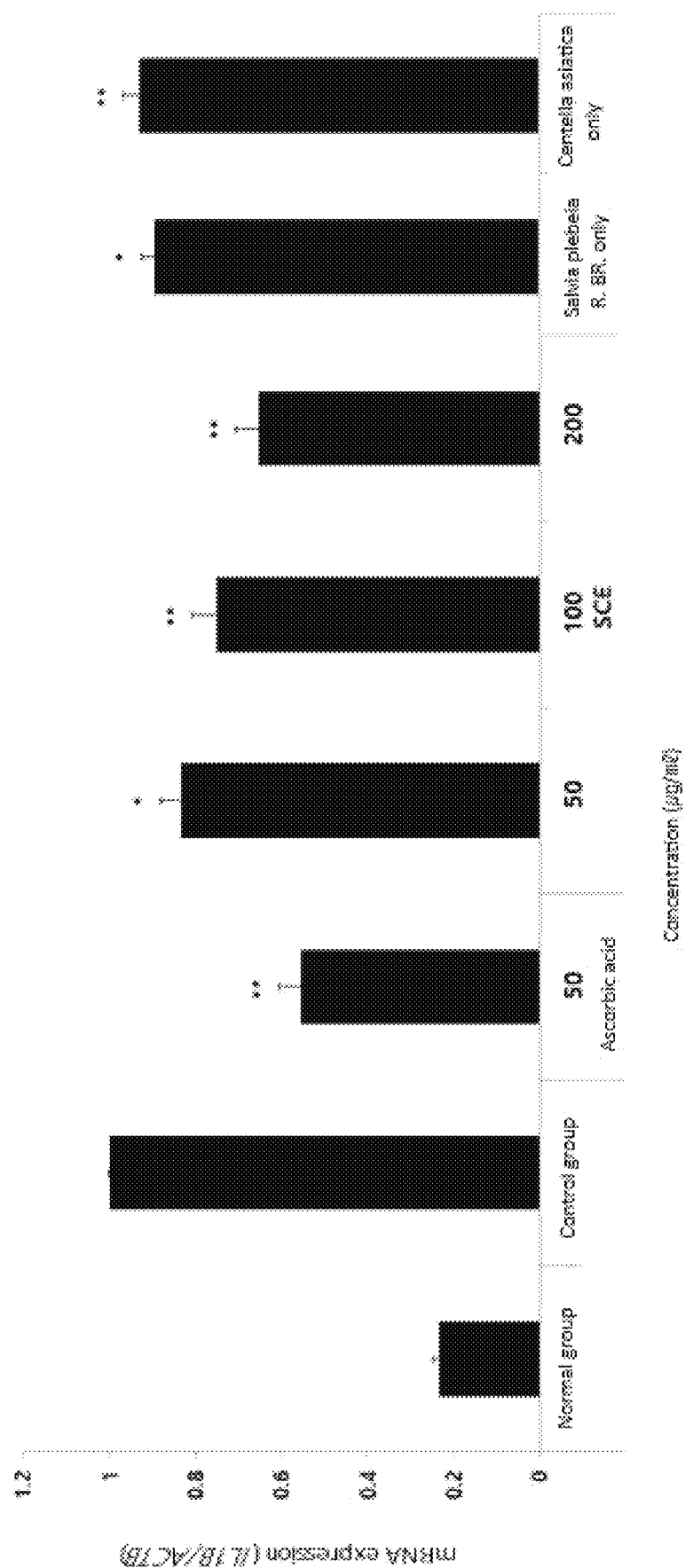
FIG. 8 is a result of measuring an mRNA expression level of IL1B gene by a mixture of Salvia plebeia R. BR. and Centella asiatica according to one embodiment of the present invention.
Figure 9:
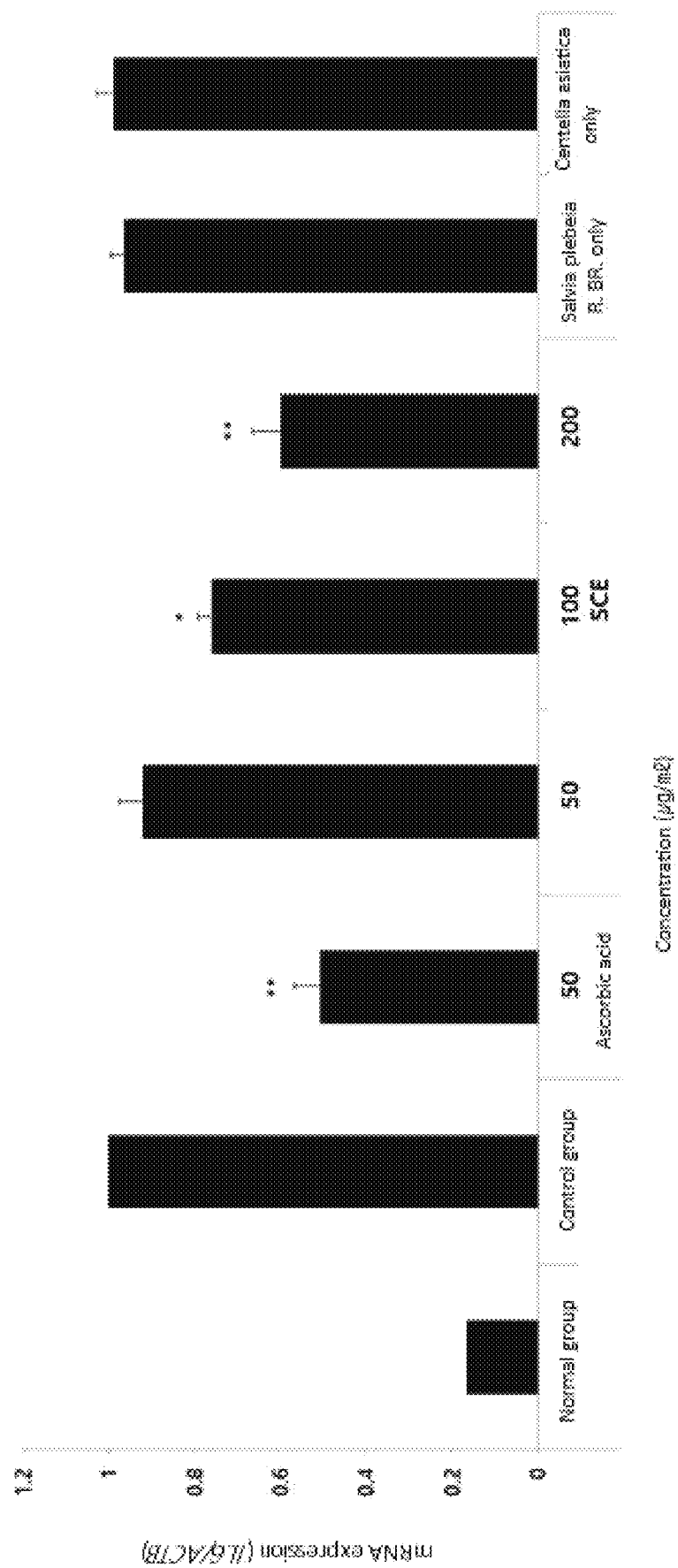
FIG. 9 is a result of measuring an mRNA expression level of IL6 gene by a mixture of Salvia plebeia R. BR. and Centella asiatica according to one embodiment of the present invention.
Figure 10:
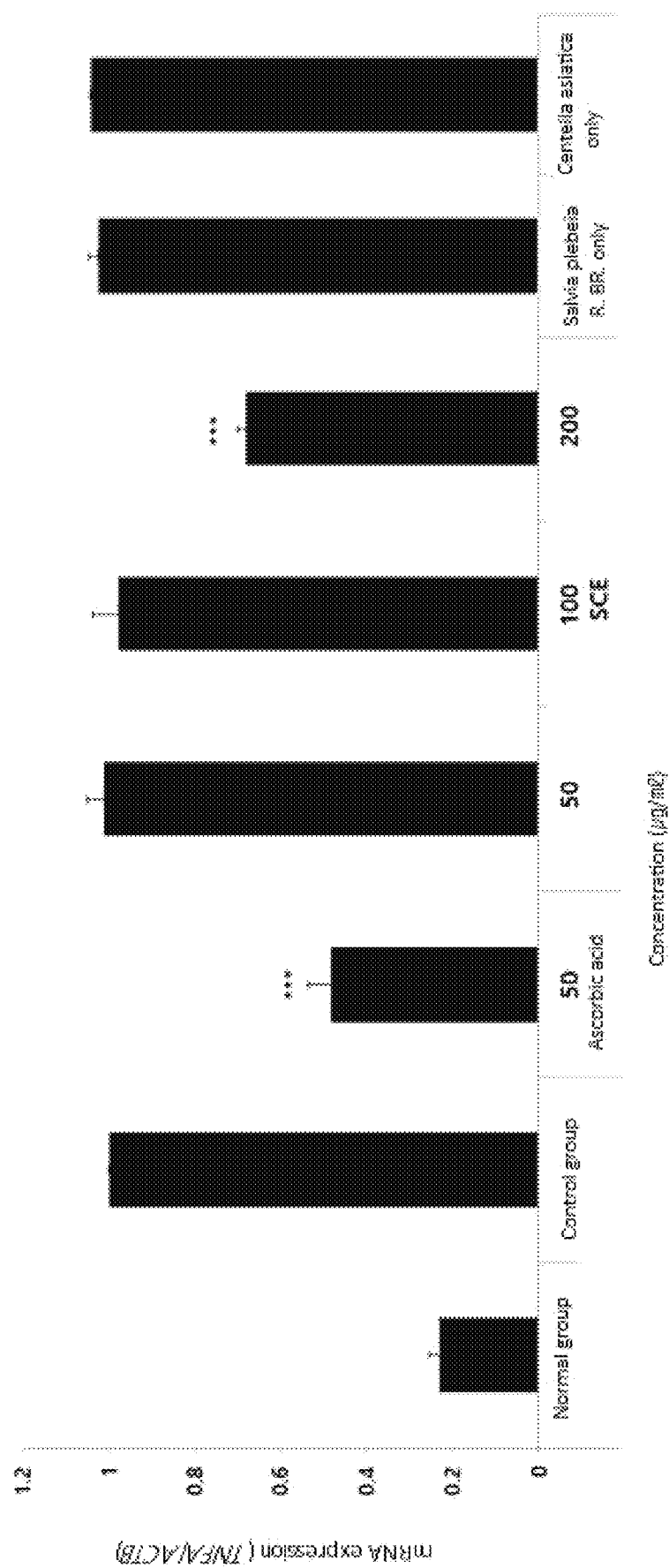
FIG. 10 is a result of measuring an mRNA expression level of TNFA gene by a mixture of Salvia plebeia R. BR. and Centella asiatica according to one embodiment of the present invention.

As a result, referring to FIG. 5, it was seen that the SCE maintains cell viability of RAW264.7 cells at a level of about 100% at a concentration of 200 µg/ml or less, and shows a slight decrease in the cell viability of RAW264.7 cells at a concentration of 400 µg/ml or more, thus confirming that there is no cytotoxicity.

In addition, the same experiment was further carried out for each individual composition of the *Salvia plebeia* R. BR. extract alone (400 µg/ml) of Example 1 and the *Centella asiatica* extract alone (400 µg/ml) of Example 2 and compared together as shown in FIG. 5.

4-2. Measurement of Gene Expression Level

RAW264.7 cells were seeded in a 6-well plate at $2 \times 10^6$ cells/well and cultured for 24 hours. After the incubation, the cells were treated with the SCE at a concentration of 50, 100 and 200 µg/ml, treated with the LPS at 100 ng/ml in two hours later, and cultured for another 24 hours. After that, RNA was extracted from the cells by using a total RNA prep kit (Intronbio, Korea). 1 ml of easy blue and 200 µl of chloroform were added to the cells obtained by centrifugation at 1, 200 rpm for five minutes, subjected to vortexing, and centrifuged at 13,000 rpm, 4° C. for 10 minutes. After 400 µl of the supernatant and 400 µl of binding buffer were reacted at room temperature for one minute, after which 700 µl of the reaction solution was injected into a column and centrifuged at 13,000 rpm for 30 seconds. 700 μl of washing buffer A was added to the column and centrifuged at 13,000 rpm for 30 seconds, after which 700 μl of washing buffer B was added and centrifuged in the same manner. After replacing the bottom of the column with a 1.5 ml tube, 30 μl of elution buffer was added to the column, reacted for one minute, and centrifuged at 13,000 rpm for one minute to extract total RNA.

A reverse transcription reaction was performed by adding 1 μg of total RNA to a mixture of accupower cyclescript RT premix kit (Bioneer, Korea) (including reaction buffer, dNTPs mixture, RNase inhibitor, stabilizer, and oligo-dT15 primer), and DEPCDW was added to make a final volume of 20 μl. The resulting mixture was mixed well, reacted at 45° C. for 60 minutes to synthesize first-strand cDNA, and left to stand at 95° C. for five minutes, thereby inactivating M-MLVRT (reverse transcriptase) and using the synthesized cDNA for a polymerase chain reaction (PCR).

In order to amplify the synthesized cDNA, real-time PCR was performed, and 1 μl of cDNA, 2 μl of each primer, 10 μl of SYBR Green (Qiagen, Germany), and 5 μl of DEPC-DW were put into a real-time dedicated tube, reacted at 95° C. for two minutes, and repeated 40 times at 95° C. for five seconds and 62.5° C. for 30 seconds to amplify genes. A gene expression level was calculated compared to the control group, and the sequences of the primers used are shown in table 1 below.

TABLE 1

| Gene | Primer | Primer sequence (5'-3') |
| --- | --- | --- |
| NOS2 | Forward | CGAAACGCTTCACTTCCAA |
|  | Reverse | TGAGCCTATATTGCTGTGGCT |
| PTGS2 | Forward | AACCGCATTGCCTCTGAAT |
|  | Reverse | CATGTTCCAGGAGGATGGAG |
| IL1B | Forward | AAGAAGAGCCCATCCTCTGT |
|  | Reverse | GGAGCCTGTAGTGCAGTTGT |
| IL6 | Forward | AGTCCTTCCTACCCCAATTTCC |
|  | Reverse | GGTCTTGGTCCTTAGCCACT |
| TNFA | Forward | ATGGCCTCCCTCTCATCAGT |
|  | Reverse | TTTGCTACGACGTGGGCTAC |
| ACTB | Forward | AACCGCATTGCCTCTGAAT |
|  | Reverse | CATGTTCCAGGAGGATGGAG |

Experimental results were expressed as mean±standard error of mean by using SPSS 210, a multiple comparison was made by using ANOVA, and significance at $p<0.05$, $p<0.01$, and $p<0.001$ levels was tested through Tukey's HSD test. After that, the significance of the experimental results was tested in the same way.

As a result, referring to FIGS. 6 to 10, it was seen that the SCE decreases an mRNA expression level of itch-inducing NO synthetase (NOS2), prostaglandin synthetase (PTGS2), IL-1B, IL-6 and TNF-a genes in a concentration-dependent way.

In addition, the same experiment was further carried out for each individual composition of the *Salvia plebeia* R. BR. extract alone (200 μg/ml) of Example 1 and *Centella asiatica* extract alone (200 μg/ml) of Example 2 and compared together as shown in FIGS. 6 to 10.

4-3. Measurement of Protein Expression Level

RAW264.7 cells were seeded in a 6-well plate at $2\times10^6$ cells/well and cultured for 24 hours. After the incubation, the cells were treated with the SCE at a concentration of 50, 100 and 200 μg/ml, treated with the LPS at 100 ng/ml in two hours later, and cultured for another 24 hours. After that, the cells obtained by centrifugation at 1,200 rpm for five minutes were washed twice with D-PBS, and proteins were extracted by adding RIPA buffer (Thermo Fisher, USA) containing protease inhibitor cocktail I (Sigma-Aldrich, USA) and phosphatase inhibitors II and III. The extracted proteins were quantified by using a BCA protein quantification kit (Thermo Fisher, USA) and prepared by being mixed with a loading buffer and reacted at 95° C. for five minutes. The prepared proteins were separated for each size by SDS-PAGE through 10% acrylamide gel and transferred to a PVDF membrane. The protein-transferred membrane was immersed in 3% BSA and reacted at room temperature for two hours. After washing with TBS-T buffer, p44/42 MAPK (Erk1/2) (137F5) Rabbit mAb (Cell signaling, USA; the same hereinafter), Phospho-p44/42 MAPK (Erk1/2) (Thr202/Tyr204) (D13.14.4E) XP® Rabbit mAb, SAPK/JNK antibody, Phospho-SAPK/JNK (Thr183/Tyr185) (G9) Mouse mAb, p38 MAPK antibody or Phospho-p38 MAPK (Thr180/Tyr182) (D3F9) XP® Rabbit mAb were added as primary antibodies and reacted at 4° C. for 16 hours. After washing again three times, a secondary antibody (Jackson immunoresearch, USA) was added and reacted at room temperature for one hour and washed again to develop proteins through ECL solution. After that, a protein expression level was analyzed through chemidoc fusion FX (Vilber Lourmat, France).

Figure 11:
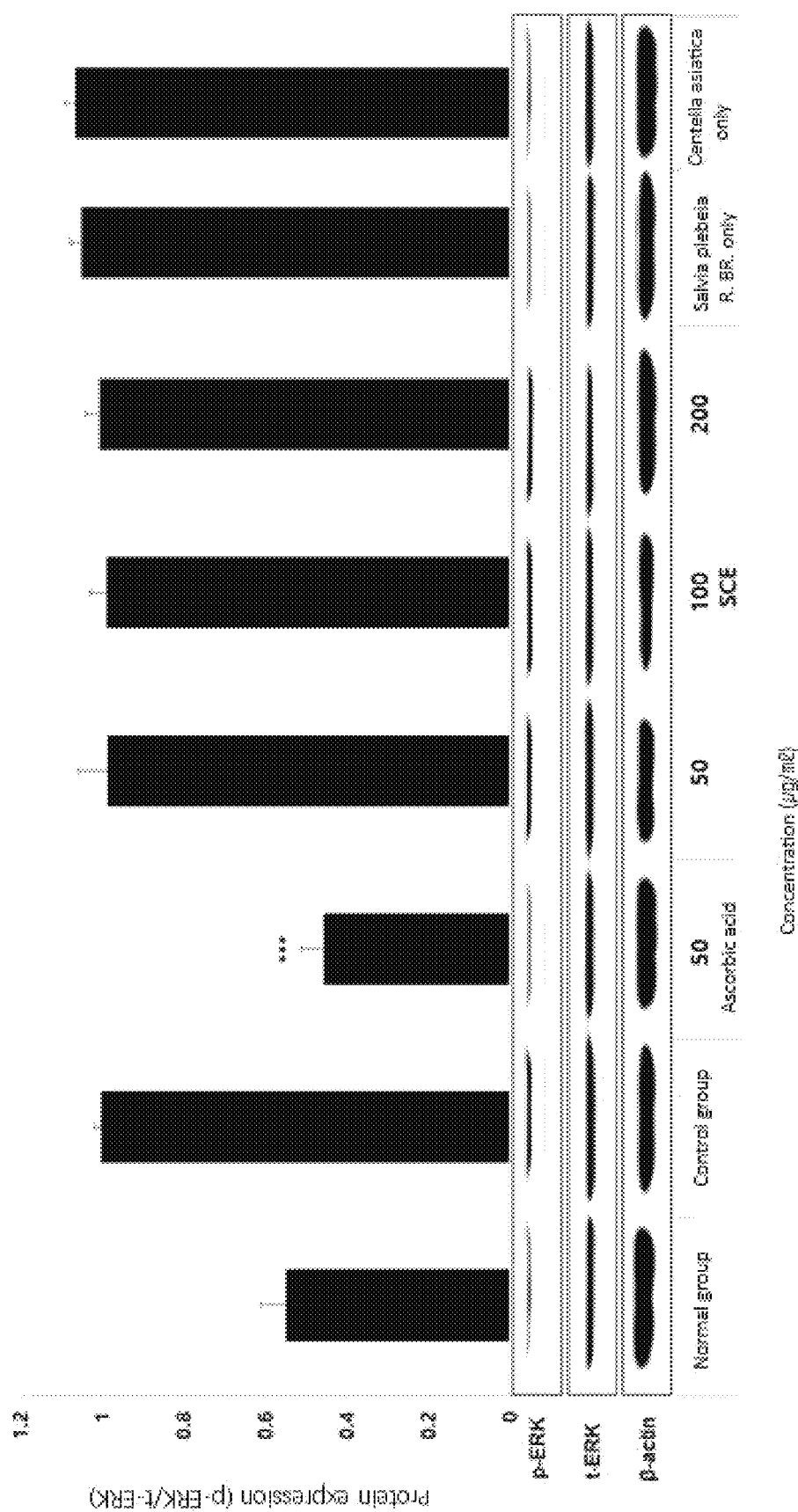
FIG. 11 is a result of measuring a protein expression level of ERK by a mixture of Salvia plebeia R. BR. and Centella asiatica according to one embodiment of the present invention.
Figure 12:
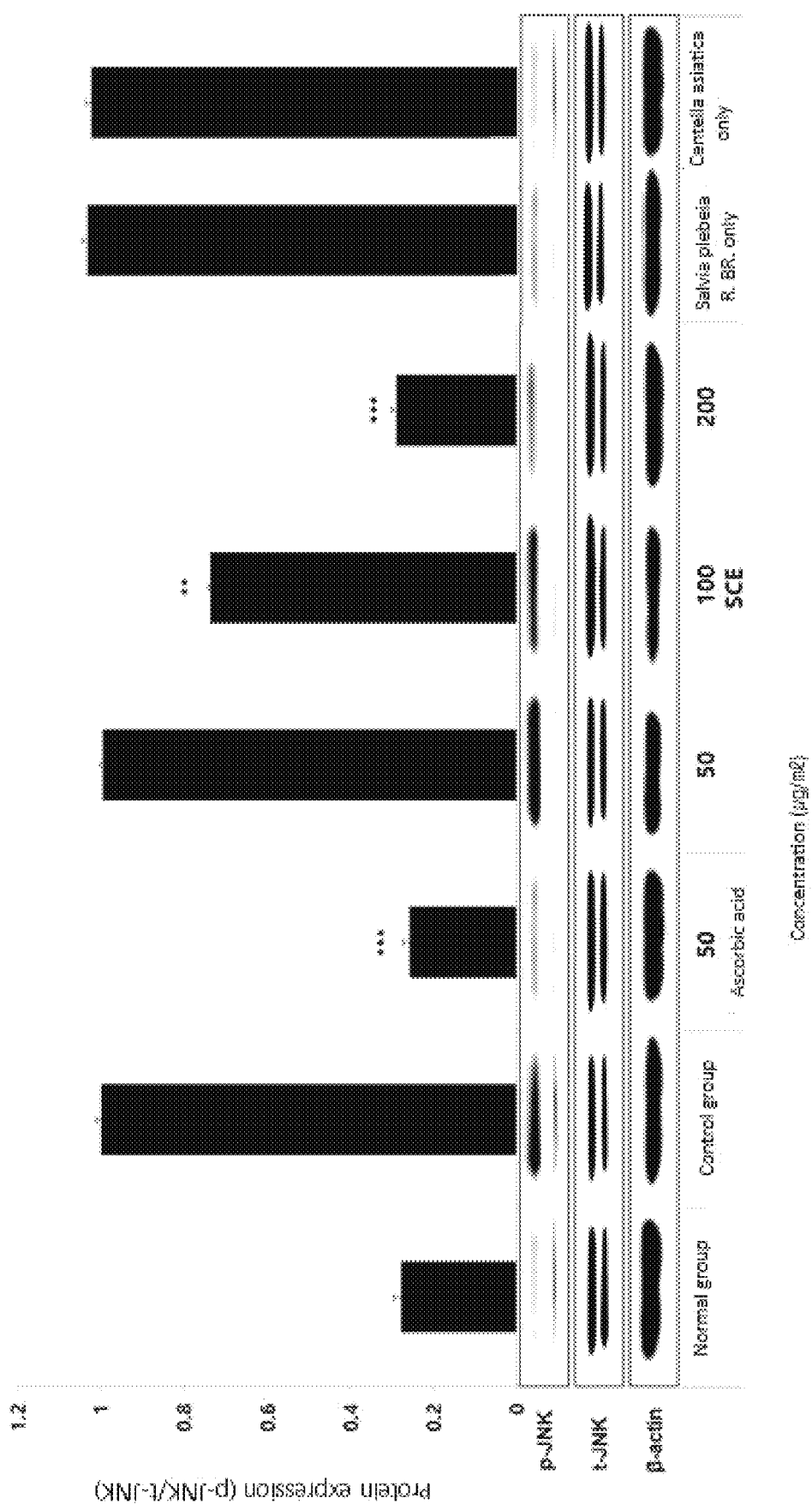
FIG. 12 is a result of measuring a protein expression level of UNK by a mixture of Salvia plebeia R. BR. and Centella asiatica according to one embodiment of the present invention.
Figure 13:
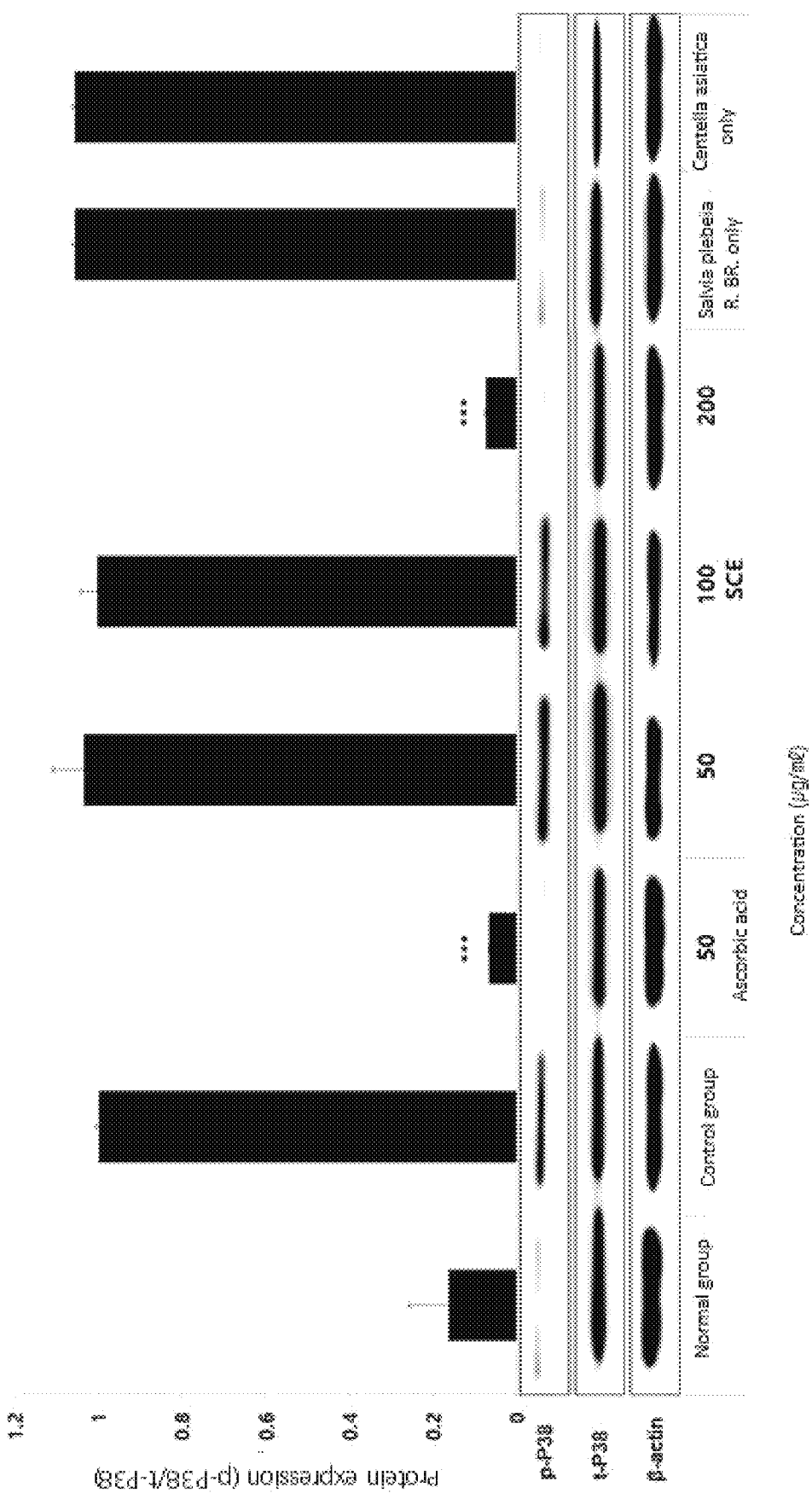
FIG. 13 is a result of measuring a protein expression level of P38 by a mixture of Salvia plebeia R. BR. and Centella asiatica according to one embodiment of the present invention.
Figure 14:
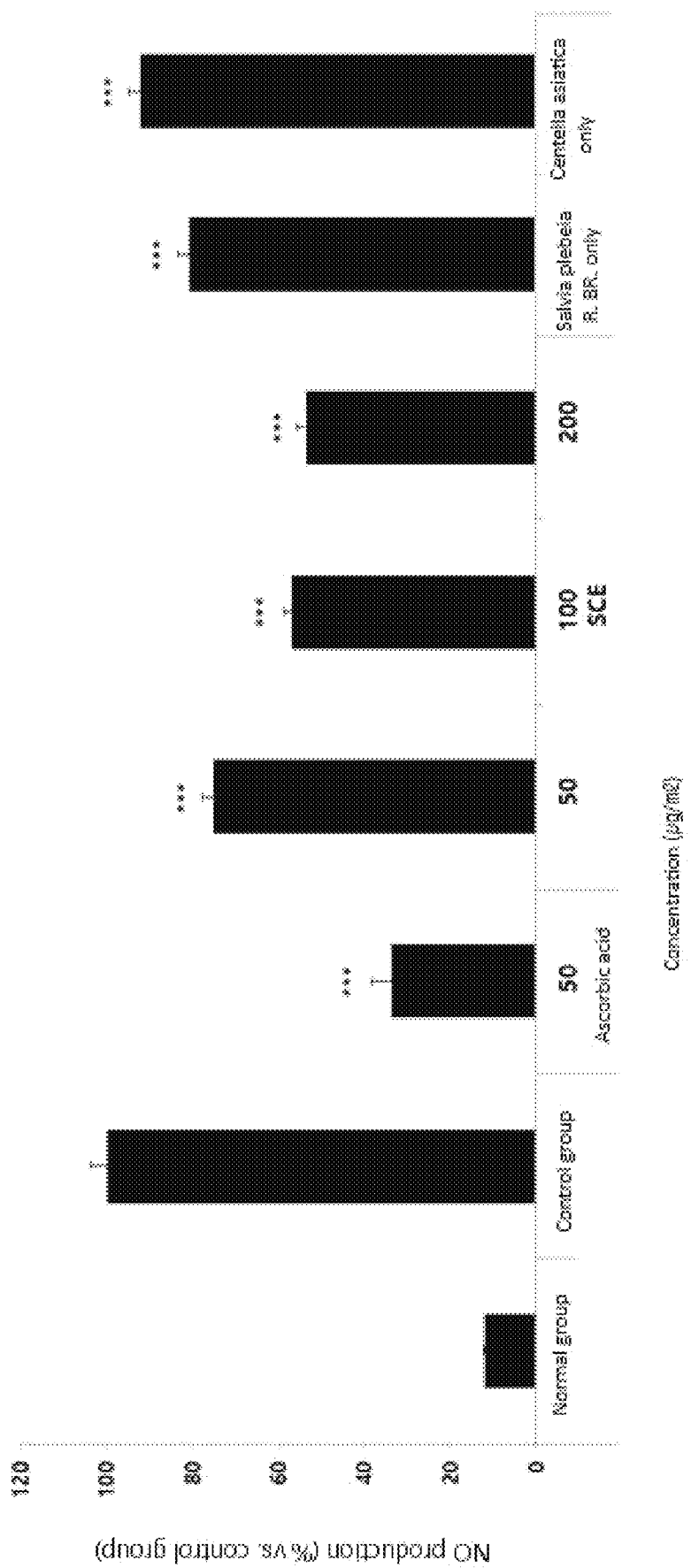
FIG. 14 is a result of measuring an amount of NO production by a mixture of Salvia plebeia R. BR. and Centella asiatica according to one embodiment of the present invention.
Figure 15:
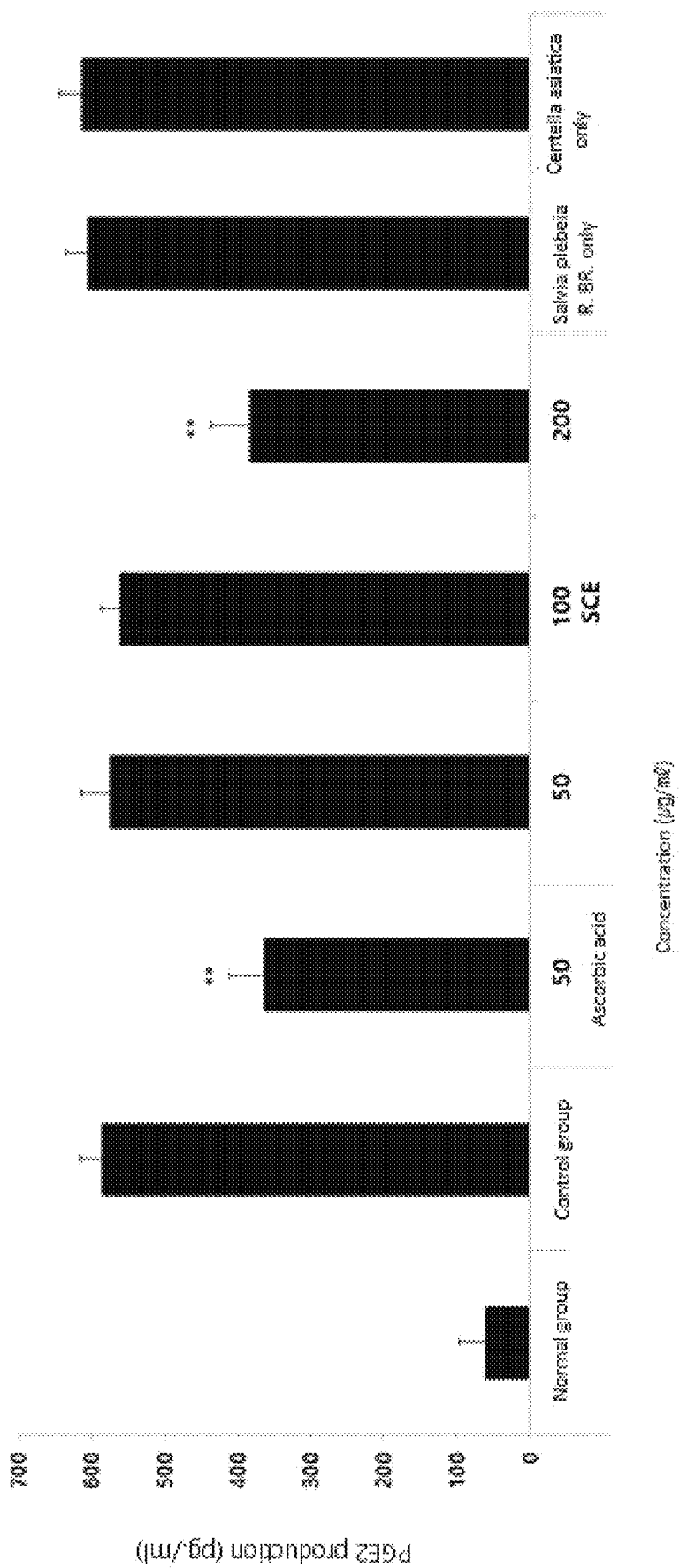
FIG. 15 is a result of measuring an amount of PGE2 production by a mixture of Salvia plebeia R. BR. and Centella asiatica according to one embodiment of the present invention.
Figure 16:
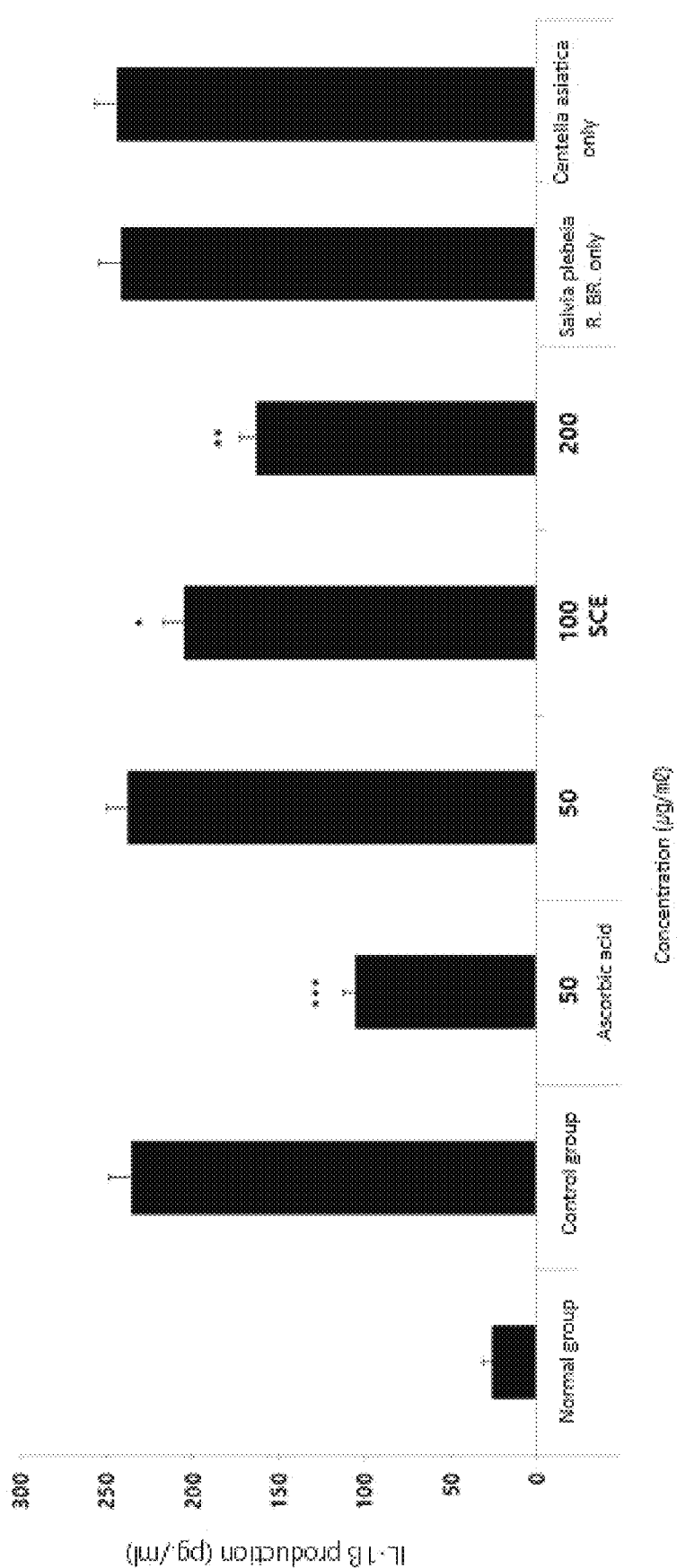
FIG. 16 is a result of measuring an amount of IL-1B production by a mixture of Salvia plebeia R. BR. and Centella asiatica according to one embodiment of the present invention.
Figure 17:
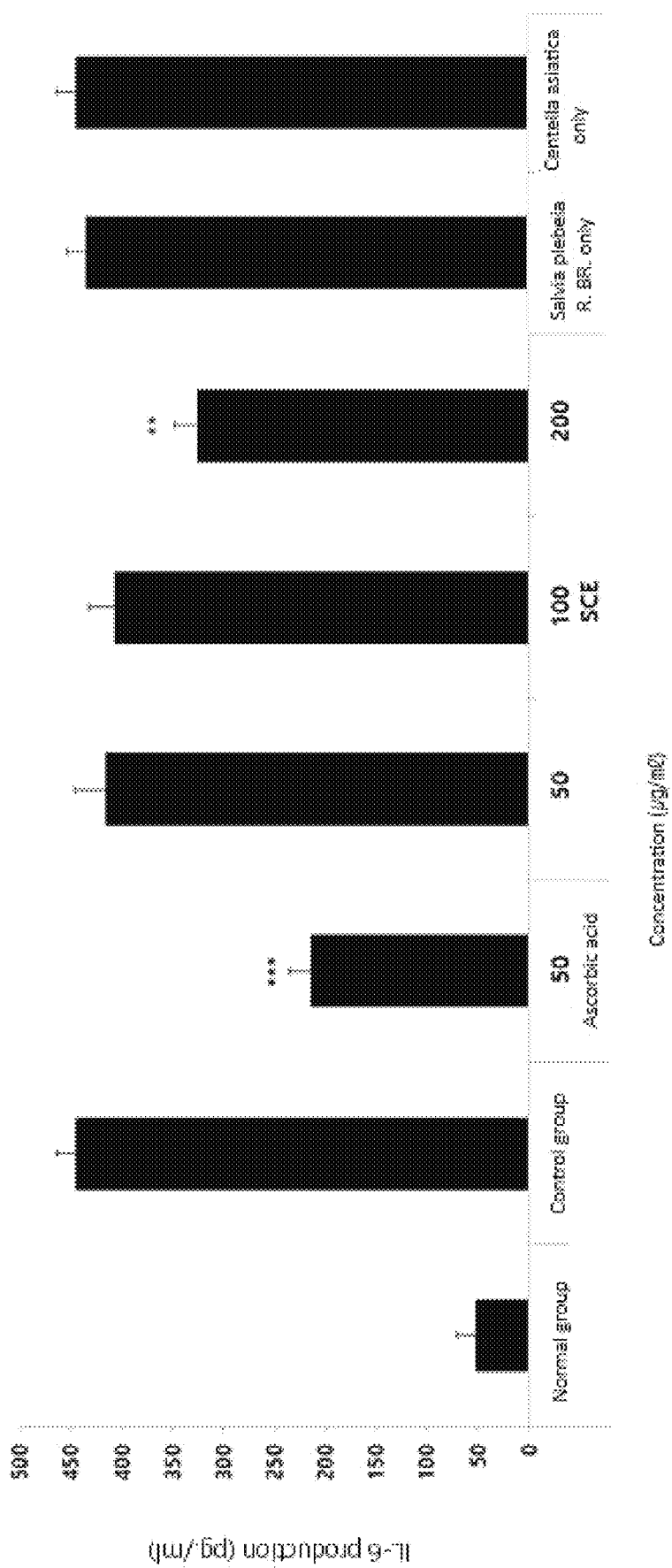
FIG. 17 is a result of measuring an amount of IL-6 production by a mixture of Salvia plebeia R. BR. and Centella asiatica according to one embodiment of the present invention.
Figure 18:
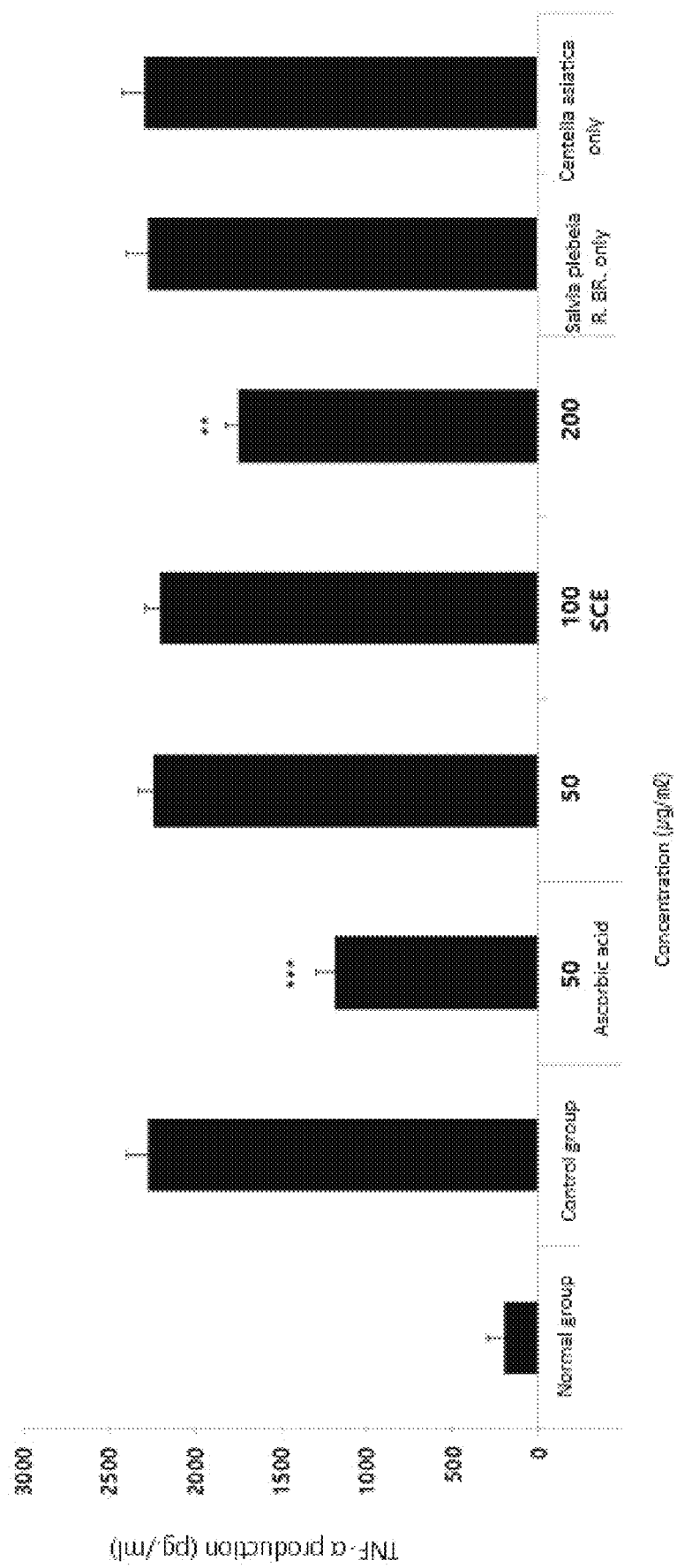
FIG. 18 is a result of measuring an amount of TNF-a production by a mixture of Salvia plebeia R. BR. and Centella asiatica according to one embodiment of the present invention.

As a result, referring to FIGS. 11 to 13, it was found that the SCE reduces the protein expression levels of ERK, JNK and P38 involved in the expression of pro-inflammatory factors such as cytokines, nitric oxide, prostaglandin, etc., in a concentration-dependent manner.

In addition, the same experiment was further carried out for each individual composition of the *Salvia plebeia* R. BR. extract alone (200 μg/ml) of Example 1 and *Centella asiatica* extract alone (200 μg/ml) of Example 2 and compared together as shown in FIGS. 11 to 13.

4-4. Measurement of Biomarker Amount

In order to measure an amount of NO production, a NO analysis kit (Intronbio, Korea) was used. RAW264.7 cells were seeded in a 24-well plate at $1\times10^5$ cells/well, cultured for 24 hours, treated with the SCE at a concentration of 50, 100, and 200 μg/ml, treated with 100 ng/ml of LPS in two hours later, and cultured again for 24 hours. After incubation, 100 μl of the cell culture fluid was added to a 96-well plate, after which 50 μl of N1 buffer was added and reacted at room temperature for 10 minutes. After the reaction, 50 μl of N2 buffer was added and reacted at room temperature for 10 minutes. After the reaction, a change in absorbance at 540 nm was measured, and a production amount relative to the control group was expressed as percentage.

In order to measure a production amount of PGE2, IL-1β, IL-6 and TNF-a, mouse PGE2 ELISA kit (R&D Systems, USA), mouse IL-1β ELISA kit (Komabiotech, Korea), mouse IL-6 ELISA kit (Komabiotech, Korea) and mouse TNF-a ELISA kit (Komabiotech, Korea) were used. RAW264.7 cells were seeded in a 6-well plate at $2\times10^6$ cells/well, cultured for 24 hours, treated with the SCE at a concentration of 50, 100, and 200 μg/ml, treated with 100 ng/ml of LPS in two hours later, and cultured again for 24 hours. After that, 100 μl of the cell culture fluid obtained by centrifugation at 1,200 rpm for five minutes was added and reacted at room temperature for two hours. After the reaction, the reagent on the plate was discarded, after which washing buffer was added and washed four times. After washing, 100 μl of detection antibody was added and reacted at room temperature for two hours. After the reaction, 100 μl of streptavidin-HRP was added to the plate and reacted at room temperature for 30 minutes. After the reaction, 100 μl of TMB or pink-ONE solution was added into each well and reacted for 15 minutes, after which 100 μl of stop solution was added and absorbance was measured at 450 nm through a microplate reader, and expressed as an absolute value based on a standard curve.

As a result, referring to FIGS. 14 to 18, it was seen that the SCE decreases a production amount of NO, PGE2, IL-1β, IL-6 and TNF-a in a concentration-dependent way.

In addition, the same experiment was further carried out for each individual composition of the *Salvia plebeia* R. BR. extract alone (200 μg/ml) of Example 1 and *Centella asiatica* extract alone (200 μg/ml) of Example 2 and compared together as shown in FIGS. 14 to 18.

Experimental Example 5. Anti-Itching Efficacy of *Salvia plebeia* R. BR and *Centella asiatica*

By using mast cells, MC/9 cells, the gene and protein expression levels of cytotoxicity and itch-inducing factors of the *Salvia plebeia* R. BR. and *Centella asiatica* mixture were measured.

5-1. Cytotoxicity

MC/9 cells were incubated in a cell incubator maintained at 37° C. and under 5% CO2 conditions by using a DMEM medium (Gibco BRL, USA) containing 10% FBS, 10% T-stim, 0.05 mM, 2-mercaptoethanol (Gibco BRL, USA), 2 mM L-glutamine and 100 μg/ml penicillin-streptomycin, after which an experiment was performed by subculture at a cycle of 2-3 days.

After that, MC/9 cells were seeded in a 48-well plate at $1\times10^5$ cells/well and cultured for 24 hours. In 24 hours later, the cells were treated with the SCE at a concentration of 10, 20, 40, and 50 μg/ml, and cultured for another 24 hours. As a positive control group of the sample, the cells were treated with ascorbic acid and treated with distilled as a negative control. After incubation, 10 μl of an EZ-Cytox solution (Daeilab, Korea) was added per 100 μl of the culture fluid and reacted for 30 minutes in a cell incubator. After the reaction, a change in absorbance at 450 nm was measured, and cell viability relative to the control group was expressed as a percentage.

Figure 19:
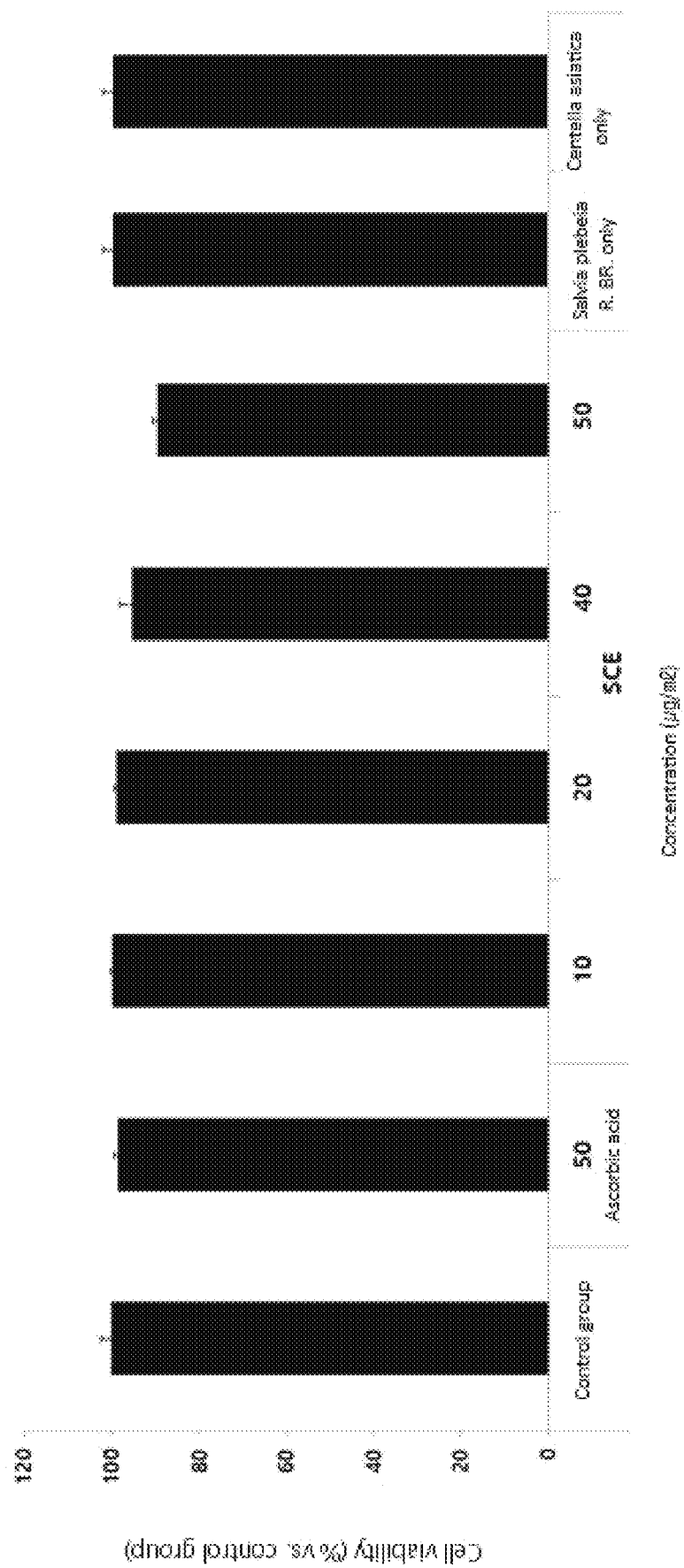
FIG. 19 is a result of measuring cell viability of MC/9 cells by a mixture of Salvia plebeia R. BR. and Centella asiatica according to one embodiment of the present invention.

As a result, referring to FIG. 19, it was seen that the SCE maintains cell viability of MC/9 cell lines at a level of about. 100% at a concentration of 40 μg/ml or less, and shows a slight decrease in the cell viability of MC/9 cell lines at a concentration of 50 μg/ml or more, thus confirming that there is no cytotoxicity.

In addition, the same experiment was further carried out for each individual composition of the *Salvia plebeia* R. BR. extract alone (50 μg/ml) of Example 1 and the *Centella asiatica* extract alone (50 μg/ml) of Example 2 and compared together as shown in FIG. 19.

5-2. Measurement of Gene Expression Level

MC/9 cells were seeded in a 6-well plate at $2\times10^6$ cells/well and cultured for 24 hours. After the incubation, the cells were treated with the SCE at a concentration of 10, 20 and 40 μg/ml, after which 1 μg/ml of DNP-IgE (Sigma-Aldrich, USA) was added in one hour later and cultured for another 12 hours. After that, total RNA extraction, CDNA synthesis, and gene amplification were performed in the same manner as in Experimental Example 4 so as to measure a gene expression level. The sequences of the primers used herein are shown in table 2 below.

TABLE 2

| Gene | Primer | Primer sequence (5'-3') |
|---|---|---|
| IL4 | Forward | CAACCCCCAGCTAGTTGTCA |
|  | Reverse | TGTCGCATCCGTGGATATGG |
| IL31 | Forward | TCAGCAGACGAATCAATACAGC |
|  | Reverse | TCGCTCAACACTTTGACTTTCT |
| ACTB | Forward | ATCGTGGGCGCCCCAGGCACCA |
|  | Reverse | GGGGTACTTCAGGGTGAGGA |

Figure 20:
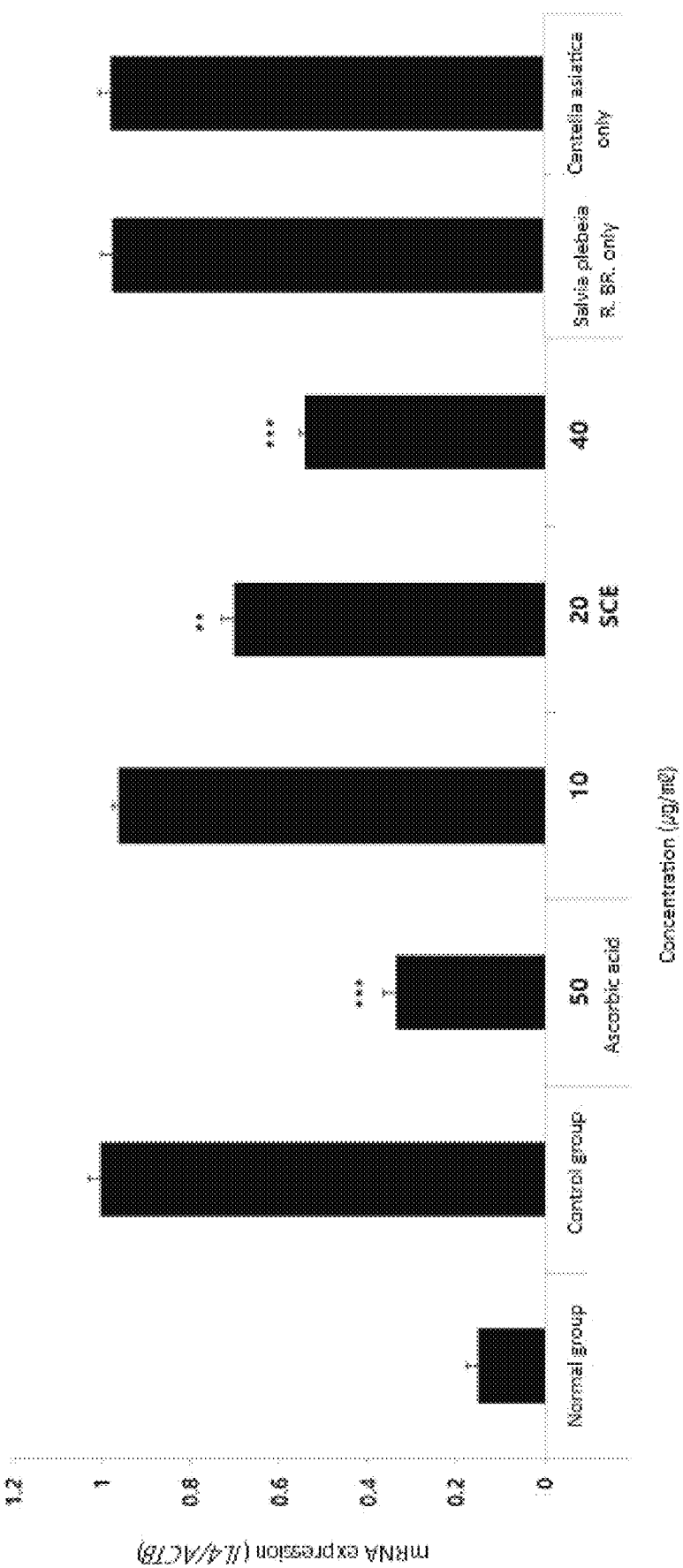
FIG. 20 is a result of measuring an mRNA expression level of IL4 gene by a mixture of Salvia plebeia R. BR. and Centella asiatica according to one embodiment of the present invention.
Figure 21:
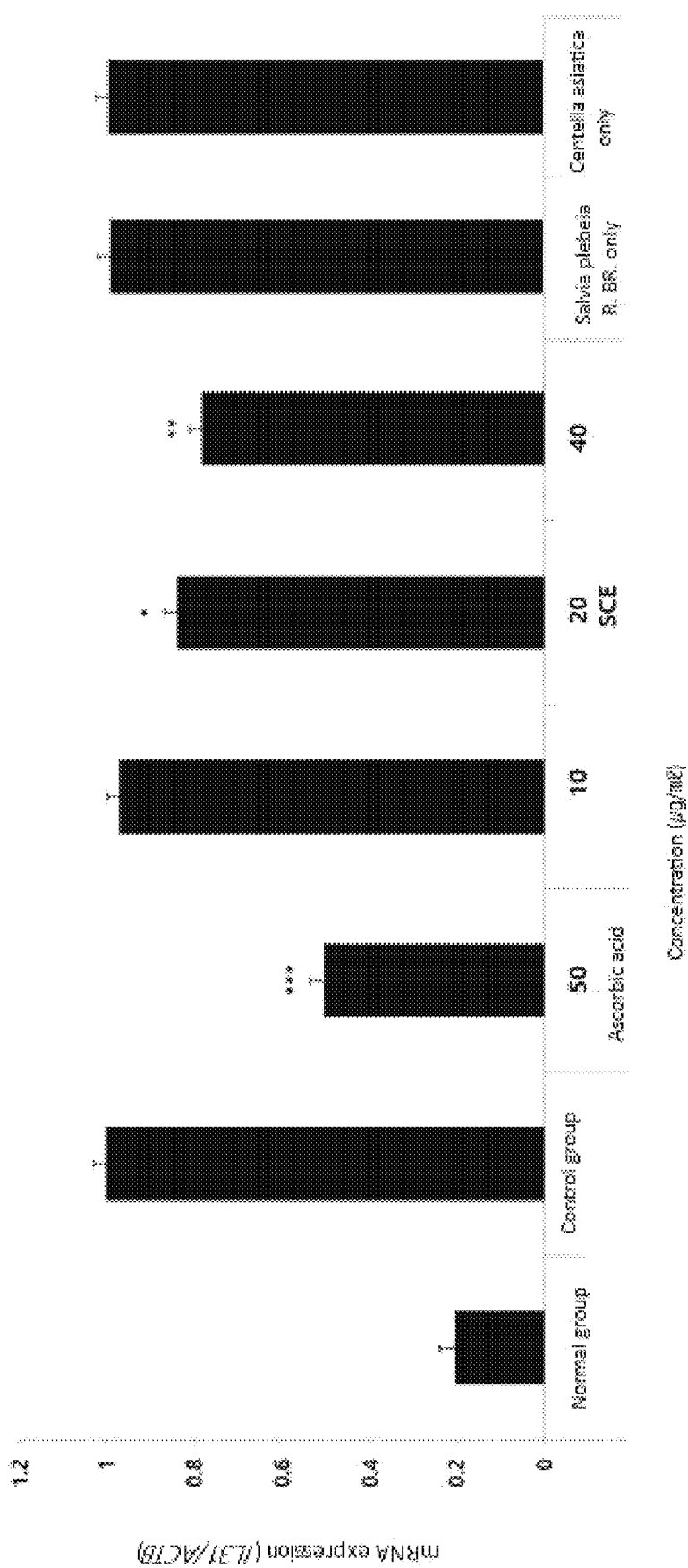
FIG. 21 is a result of measuring an mRNA expression level of IL31 gene by a mixture of Salvia plebeia R. BR. and Centella asiatica according to one embodiment of the present invention.

As a result, referring to FIGS. 20 and 21, it was seen that the SCE decreases an mRNA expression level of itch-inducing IL-4 and IL-31 genes in a concentration-dependent way.

In addition, the same experiment was further carried out. for each individual composition of the *Salvia plebeia* R. BR. extract alone (40 μg/ml) of Example 1 and *Centella asiatica* extract alone (40 μg/ml) of Example 2 and compared together as shown in FIGS. 20 and 21.

5-3. Measurement of Protein Expression Level

MC/9 cells were seeded in a 6-well plate at $2\times10^6$ cells/well and cultured for 24 hours. After the incubation, the cells were treated with the SCE at a concentration of 10, 20 and 40 μg/ml, after which 1 μg/ml of DNP-IgE was added in one hour later and cultured for another 6 hours. After that, a protein expression level was measured in the same manner as in Experimental Example 4. Herein, IL-4 antibody (Santa Cruz Biotechnology, USA), histamine antibody (LSBio, USA) or IL-31 antibody (LSBio, USA) were used as a primary antibody.

Figure 22:
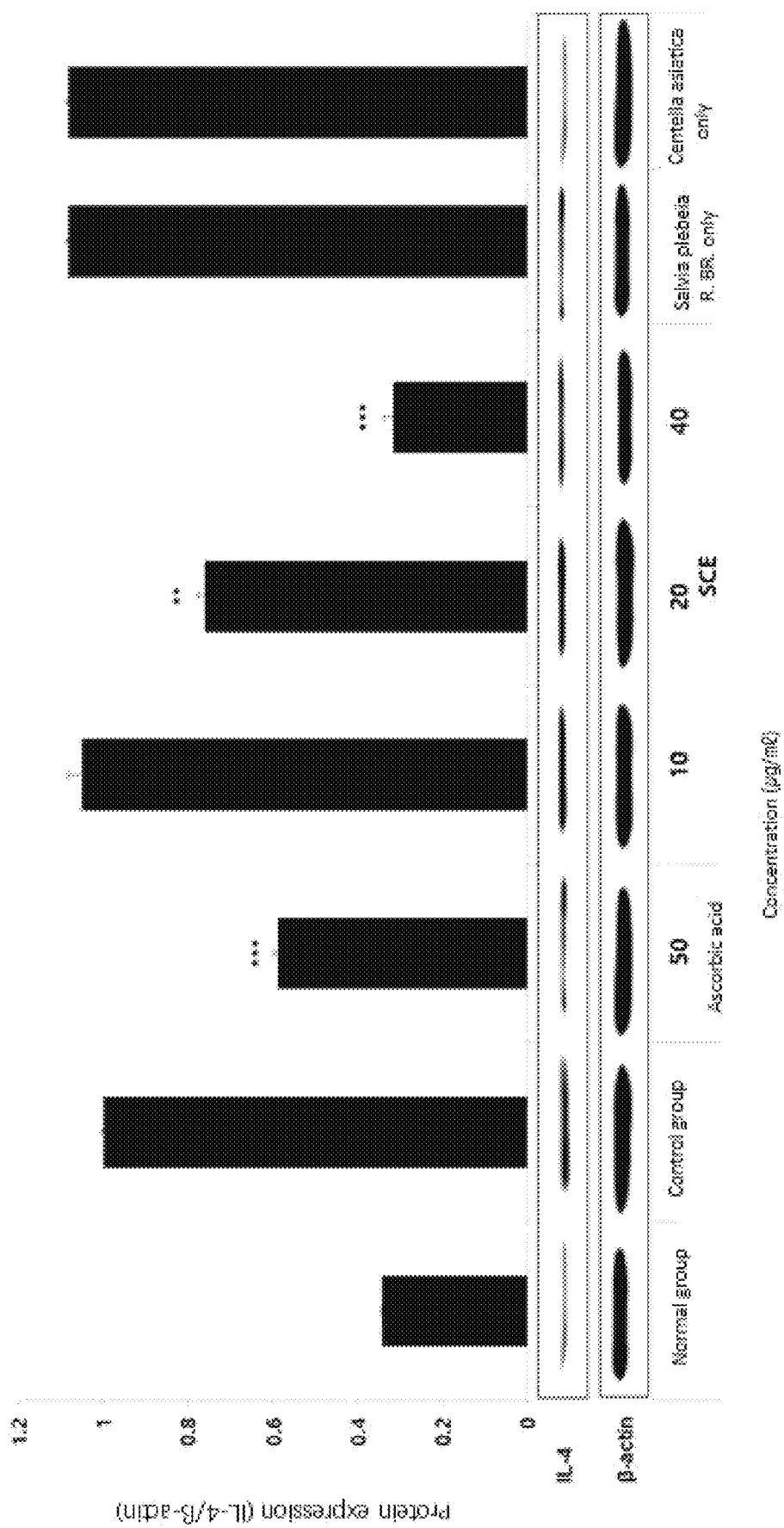
FIG. 22 is a result of measuring a protein expression level of IL-4 by a mixture of Salvia plebeia R. BR. and Centella asiatica according to one embodiment of the present invention.
Figure 23:
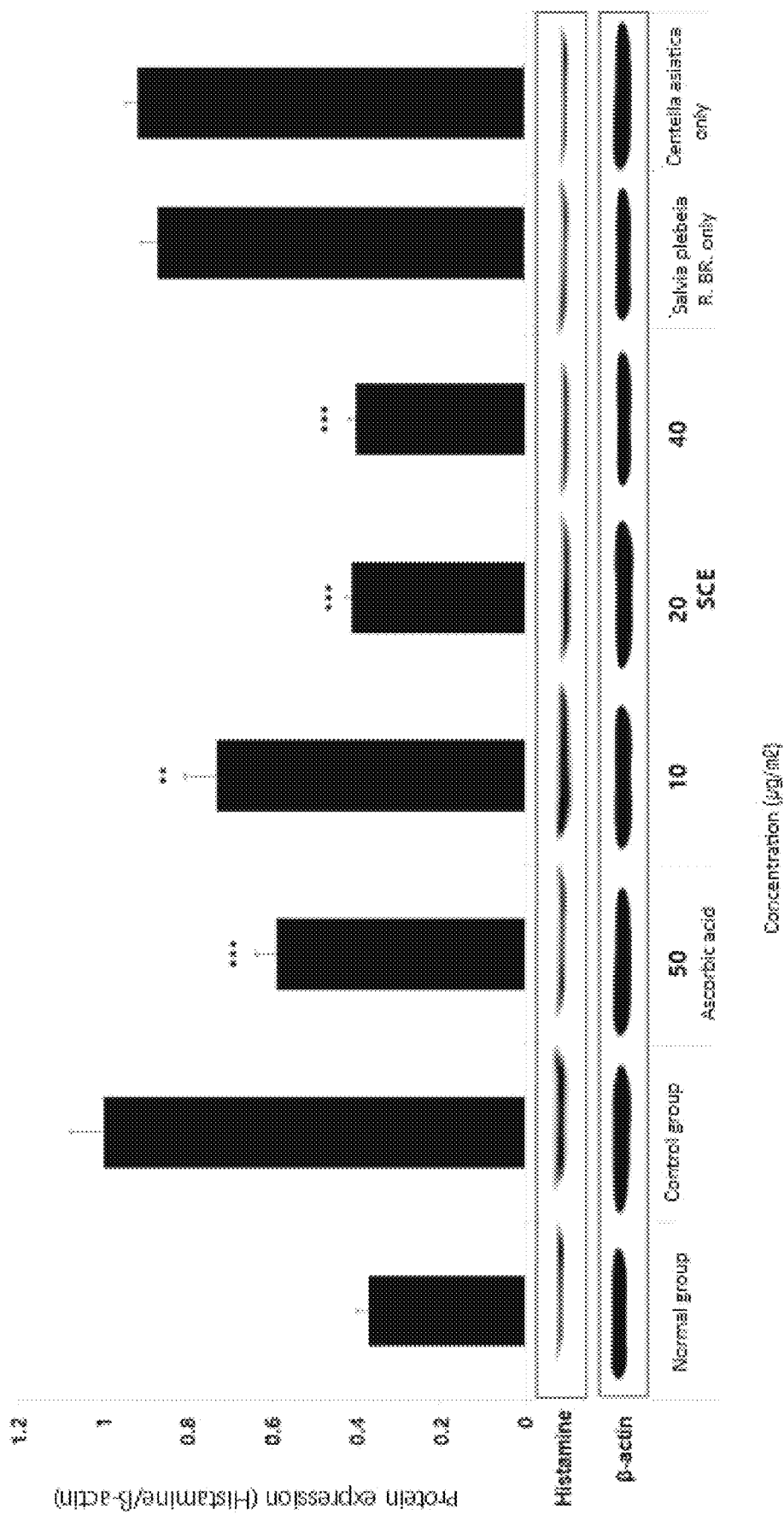
FIG. 23 is a result of measuring a protein expression level of histamine by a mixture of Salvia plebeia R. BR. and Centella asiatica according to one embodiment of the present invention.
Figure 24:
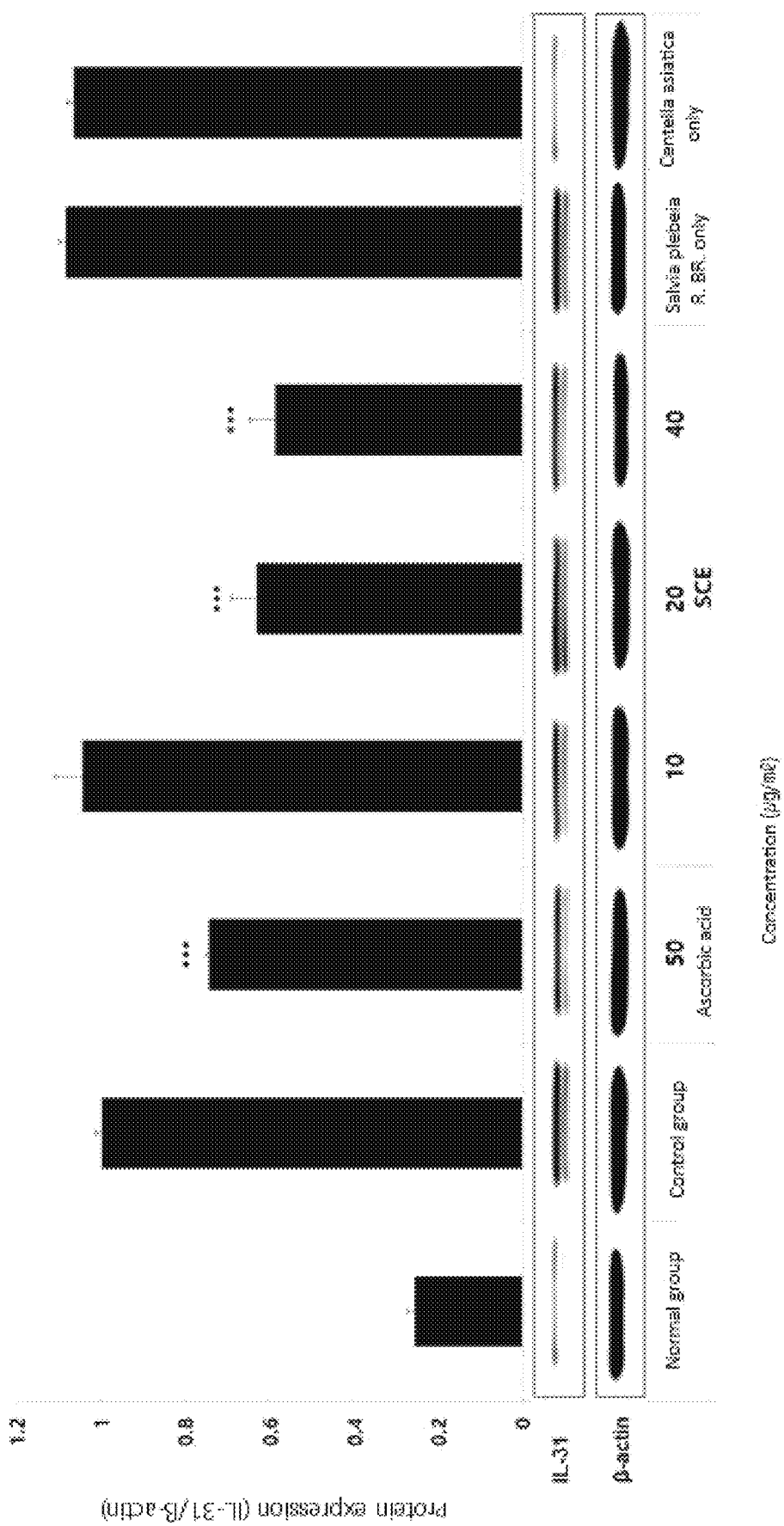
FIG. 24 is a result of measuring a protein expression level of IL-31 by a mixture of Salvia plebeia R. BR. and Centella asiatica according to one embodiment of the present invention.

As a result, referring to FIGS. 22 to 24, it was seen that the SCE decreases a protein expression level of IL-31, IL-31 and histamine in a concentration-dependent way.

In addition, the same experiment was further carried out for each individual composition of the *Salvia plebeia* R. BR. extract alone (40 μg/ml) of Example 1 and *Centella asiatica* extract alone (40 μg/ml) of Example 2 and compared together as shown in FIGS. 22 to 24.

From the above results, it is found that the *Salvia plebeia* R. BR. and *Centella asiatica* extract according to the present invention contains a large amount of total polyphenols and flavonoids to effectively remove radicals with excellent anti-oxidant efficacy and also exhibit excellent anti-inflammatory efficacy of effectively inhibiting the expression and secretion of inflammation-inducing cytokines (IL-1β and IL-6), nitric oxide and prostaglandin, and thus it is expected to be useful in effectively alleviating or relieving itchiness that may occur to the whole body including the skin and keeping a skin tone bright and clear.

Meanwhile, as a result of comparison with an experiment. conducted with each individual composition of the *Salvia plebeia* R. BR. Extract of Example 1 and the *Centella asiatica* extract of Example 2, it was seen that an SCE value shows an excellent effect compared to an experimental value for the *Salvia plebeia* R. BR. extract alone and an experimental value for the *Centella asiatica* extract alone based on the same concentration, thus confirming that an unexpected effect is obtained through mixing of constituent components.

So far, the preferred embodiments have been described with respect to the present invention. Those skilled in the art to which the present invention pertains will understand that the present invention can be implemented in a modified form without departing from the essential properties of the present invention. Thus, the disclosed embodiments are to be considered in an illustrative rather than a restrictive sense. The scope of the present invention is indicated in the claims rather than the foregoing description, and all differences within the scope equivalent thereto should be construed as being included in the present invention.

The invention claimed is:

1. A composition for anti-oxidation and anti-inflammation, comprising a *Salvia plebeia* R. BR. extract and a *Centella asiatica* extract as an active ingredient in a weight ratio of 7:3,
   wherein the *Salvia plebeia* R. BR. extract is obtained by adding 70% ethanol to freeze-dried *Salvia plebeia* R. BR. leaves and stems, performing reflux extraction for 1 to 5 hours, concentrating under reduced pressure using a rotary vacuum evaporator, and freeze-drying with a freeze dryer, and
   wherein the *Centella asiatica* extract is obtained by adding 70% ethanol to freeze-dried *Centella asiatica* leaves and petioles, performing reflux extraction for 1 to 5 hours, concentrating under reduced pressure using a rotary vacuum evaporator, and freeze-drying with a freeze dryer.

2. The composition of claim 1, wherein the composition is for skin, scalp, oral cavity, eye or vagina.

3. A cosmetic composition for anti-oxidation and anti-inflammation, comprising the composition of claim 2.

4. The composition of claim 3, wherein the cosmetic composition is to alleviate or relieve skin itchiness.

5. The composition of claim 3, wherein the cosmetic composition is to brighten a skin tone.

6. A cosmetic composition for anti-oxidation and anti-inflammation, comprising the composition of claim 1.

* * * * *

```
                       SEQUENCE LISTING

<160> NUMBER OF SEQ ID NOS: 18

<210> SEQ ID NO 1
<211> LENGTH: 19
<212> TYPE: DNA
<213> ORGANISM: Mus musculus

<400> SEQUENCE: 1
cgaaacgctt cacttccaa                                                   19

<210> SEQ ID NO 2
<211> LENGTH: 21
<212> TYPE: DNA
<213> ORGANISM: Mus musculus

<400> SEQUENCE: 2
tgagcctata ttgctgtggc t                                                21

<210> SEQ ID NO 3
<211> LENGTH: 19
<212> TYPE: DNA
<213> ORGANISM: Mus musculus

<400> SEQUENCE: 3
aaccgcattg cctctgaat                                                   19

<210> SEQ ID NO 4
<211> LENGTH: 20
<212> TYPE: DNA
<213> ORGANISM: Mus musculus

<400> SEQUENCE: 4
catgttccag gaggatggag                                                  20

<210> SEQ ID NO 5
<211> LENGTH: 20
<212> TYPE: DNA
<213> ORGANISM: Mus musculus

<400> SEQUENCE: 5
aagaagagcc catcctctgt                                                  20

<210> SEQ ID NO 6
<211> LENGTH: 20
<212> TYPE: DNA
<213> ORGANISM: Mus musculus

<400> SEQUENCE: 6
ggagcctgta gtgcagttgt                                                  20

<210> SEQ ID NO 7
<211> LENGTH: 22
<212> TYPE: DNA
<213> ORGANISM: Mus musculus

<400> SEQUENCE: 7
agtccttcct accccaattt cc                                               22

<210> SEQ ID NO 8
<211> LENGTH: 20
<212> TYPE: DNA
```

```
<213> ORGANISM: Mus musculus

<400> SEQUENCE: 8
ggtcttggtc cttagccact                                               20

<210> SEQ ID NO 9
<211> LENGTH: 20
<212> TYPE: DNA
<213> ORGANISM: Mus musculus

<400> SEQUENCE: 9
atggcctccc tctcatcagt                                               20

<210> SEQ ID NO 10
<211> LENGTH: 20
<212> TYPE: DNA
<213> ORGANISM: Mus musculus

<400> SEQUENCE: 10
tttgctacga cgtgggctac                                               20

<210> SEQ ID NO 11
<211> LENGTH: 19
<212> TYPE: DNA
<213> ORGANISM: Mus musculus

<400> SEQUENCE: 11
aaccgcattg cctctgaat                                                19

<210> SEQ ID NO 12
<211> LENGTH: 20
<212> TYPE: DNA
<213> ORGANISM: Mus musculus

<400> SEQUENCE: 12
catgttccag gaggatggag                                               20

<210> SEQ ID NO 13
<211> LENGTH: 20
<212> TYPE: DNA
<213> ORGANISM: Mus musculus

<400> SEQUENCE: 13 caaccccag ctagttgtca                                                20

<210> SEQ ID NO 14
<211> LENGTH: 20
<212> TYPE: DNA
<213> ORGANISM: Mus musculus

<400> SEQUENCE: 14
tgtcgcatcc gtggatatgg                                               20

<210> SEQ ID NO 15
<211> LENGTH: 22
<212> TYPE: DNA
<213> ORGANISM: Mus musculus

<400> SEQUENCE: 15
tcagcagacg aatcaataca gc                                            22

<210> SEQ ID NO 16
<211> LENGTH: 22
```

-continued

```
<212> TYPE: DNA
<213> ORGANISM: Mus musculus

<400> SEQUENCE: 16
tcgctcaaca ctttgacttt ct                                            22

<210> SEQ ID NO 17
<211> LENGTH: 23
<212> TYPE: DNA
<213> ORGANISM: Mus musculus

<400> SEQUENCE: 17
atcgtggggc gccccaggca cca                                           23

<210> SEQ ID NO 18
<211> LENGTH: 20
<212> TYPE: DNA
<213> ORGANISM: Mus musculus

<400> SEQUENCE: 18
ggggtacttc agggtgagga                                               20
```